United States Patent
Yoo

(10) Patent No.: US 11,455,720 B2
(45) Date of Patent: Sep. 27, 2022

(54) APPARATUS FOR ULTRASOUND DIAGNOSIS OF LIVER STEATOSIS USING FEATURE POINTS OF ULTRASOUND IMAGE AND REMOTE MEDICAL-DIAGNOSIS METHOD USING THE SAME

(71) Applicant: HEALCERION CO., LTD., Seoul (KR)

(72) Inventor: Jae Chern Yoo, Gyeonggi-do (KR)

(73) Assignee: HEALCERION CO., LTD., Gyeonggi-do (KR)

( * ) Notice: Subject to any disclaimer, the term of this patent is extended or adjusted under 35 U.S.C. 154(b) by 519 days.

(21) Appl. No.: 16/668,140

(22) Filed: Oct. 30, 2019

(65) Prior Publication Data
US 2021/0035286 A1    Feb. 4, 2021

(30) Foreign Application Priority Data

Jul. 30, 2019 (KR) .......................... 10-2019-0092089

(51) Int. Cl.
*G06T 7/00* (2017.01)
*A61B 8/08* (2006.01)
(Continued)

(52) U.S. Cl.
CPC .......... *G06T 7/0012* (2013.01); *A61B 5/0002* (2013.01); *A61B 8/5207* (2013.01);
(Continued)

(58) Field of Classification Search
CPC ................... G06T 7/0012; G06T 7/337; G06T 2207/10132; G06T 2207/20081; G06T 2207/20084; G06T 2207/30056; G06T 7/12; G06T 7/149; A61B 5/0002; A61B 8/5207; A61B 5/4244; A61B 8/08;
(Continued)

(56) References Cited

U.S. PATENT DOCUMENTS 9,092,691 B1*   7/2015  Beaumont ............. G06T 7/0014
2010/0121156 A1*   5/2010  Yoo ........................ G16H 40/67
600/300

(Continued)

FOREIGN PATENT DOCUMENTS

EP        2140412 B1      12/2018
KR     20180070990        *  6/2018  ........... A61B 8/0825

OTHER PUBLICATIONS

Byra et al, ("Transfer learning with deep convolutional neural network for liver steatosis assessment in ultrasound images", International Journal of Computer Assisted Radiology and Surgery (2018) 13:1895-1903, pp. 1895-1903, Springer) (Year: 2018).*

(Continued)

*Primary Examiner* — Amara Abdi
(74) *Attorney, Agent, or Firm* — Harness, Dickey & Pierce, P.L.C.

(57) ABSTRACT

Disclosed herein are an apparatus for automatic ultrasound diagnosis of liver steatosis using feature points in an ultrasound image, which can automatically determine a grade of liver steatosis, which is difficult to determine visually, through extraction from an image acquired by medical imaging, and a remote medical diagnosis method using the same.

19 Claims, 14 Drawing Sheets

(51) Int. Cl.
*A61B 5/00* (2006.01)
*G06T 7/33* (2017.01)
*G06N 3/02* (2006.01)
*G06V 10/20* (2022.01)
*G06V 10/25* (2022.01)
*G06V 20/40* (2022.01)
*G06V 10/24* (2022.01)

(52) U.S. Cl.
CPC .............. *G06N 3/02* (2013.01); *G06T 7/337* (2017.01); *G06V 10/20* (2022.01); *G06V 10/25* (2022.01); *G06V 20/41* (2022.01); *G06T 2207/10132* (2013.01); *G06T 2207/20081* (2013.01); *G06T 2207/20084* (2013.01); *G06T 2207/30056* (2013.01); *G06V 10/248* (2022.01)

(58) Field of Classification Search
CPC ....... A61B 8/461; A61B 8/469; A61B 8/5223; A61B 8/085; G06N 3/02; G06N 20/10; G06N 3/0445; G06N 3/0454; G06V 10/20; G06V 10/25; G06V 20/41; G06V 10/248; G06V 10/82; G06V 2201/03; G06V 10/44; G06K 9/6268; G16H 50/20
See application file for complete search history.

(56) References Cited

U.S. PATENT DOCUMENTS

| | | | |
|---|---|---|---|
| 2014/0328517 A1* | 11/2014 | Gluncic | A61B 8/5215 382/103 |
| 2015/0062129 A1* | 3/2015 | Wilensky | G06T 11/203 345/442 |
| 2015/0086094 A1* | 3/2015 | Chang | G06T 7/0012 382/128 |
| 2018/0116726 A1* | 5/2018 | Liang | G06F 3/011 |
| 2019/0205606 A1* | 7/2019 | Zhou | G06N 3/0445 |
| 2020/0309880 A1* | 10/2020 | Bi | G01R 33/307 |
| 2021/0059762 A1* | 3/2021 | Ng | A61B 5/7425 |

OTHER PUBLICATIONS

Dan Mihai, ("Automatic evaluation of steatosis by ultrasound image analysis", IEEE 2012) (Year: 2012).*

* cited by examiner

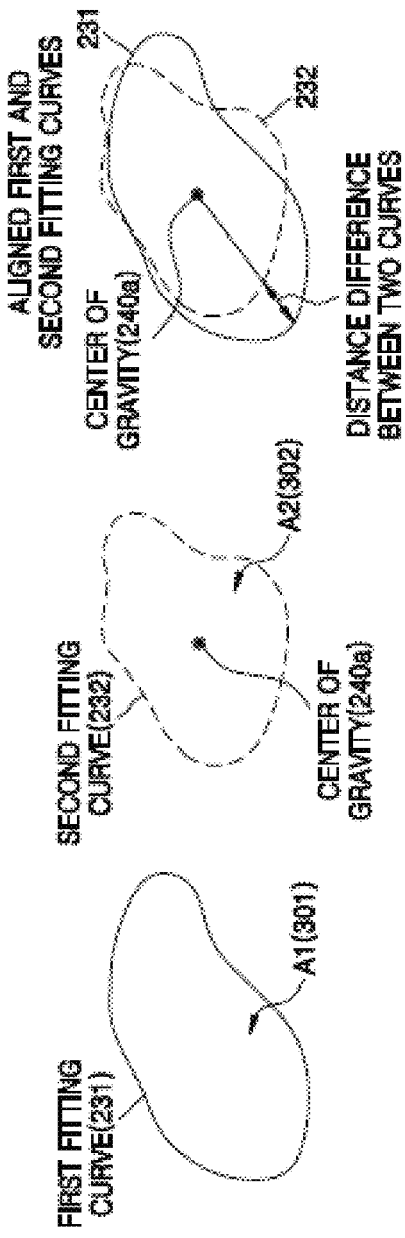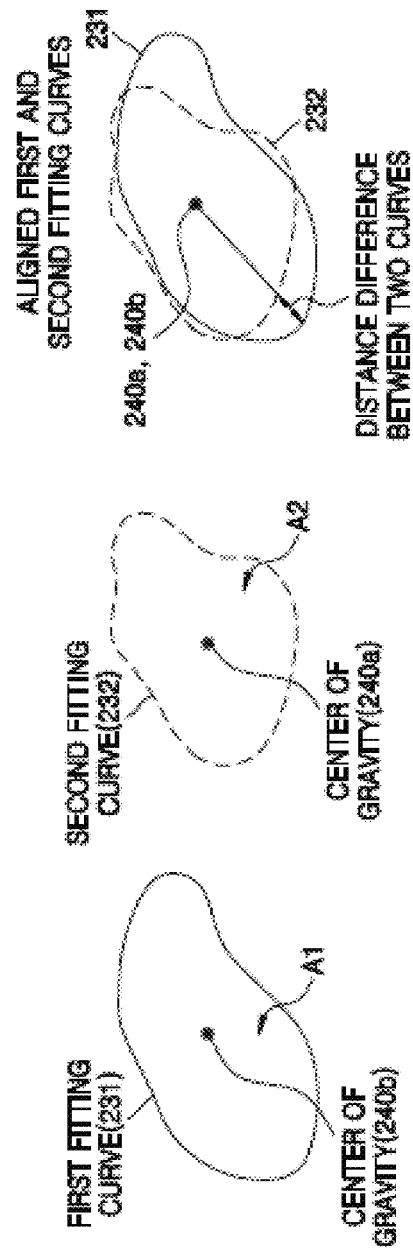

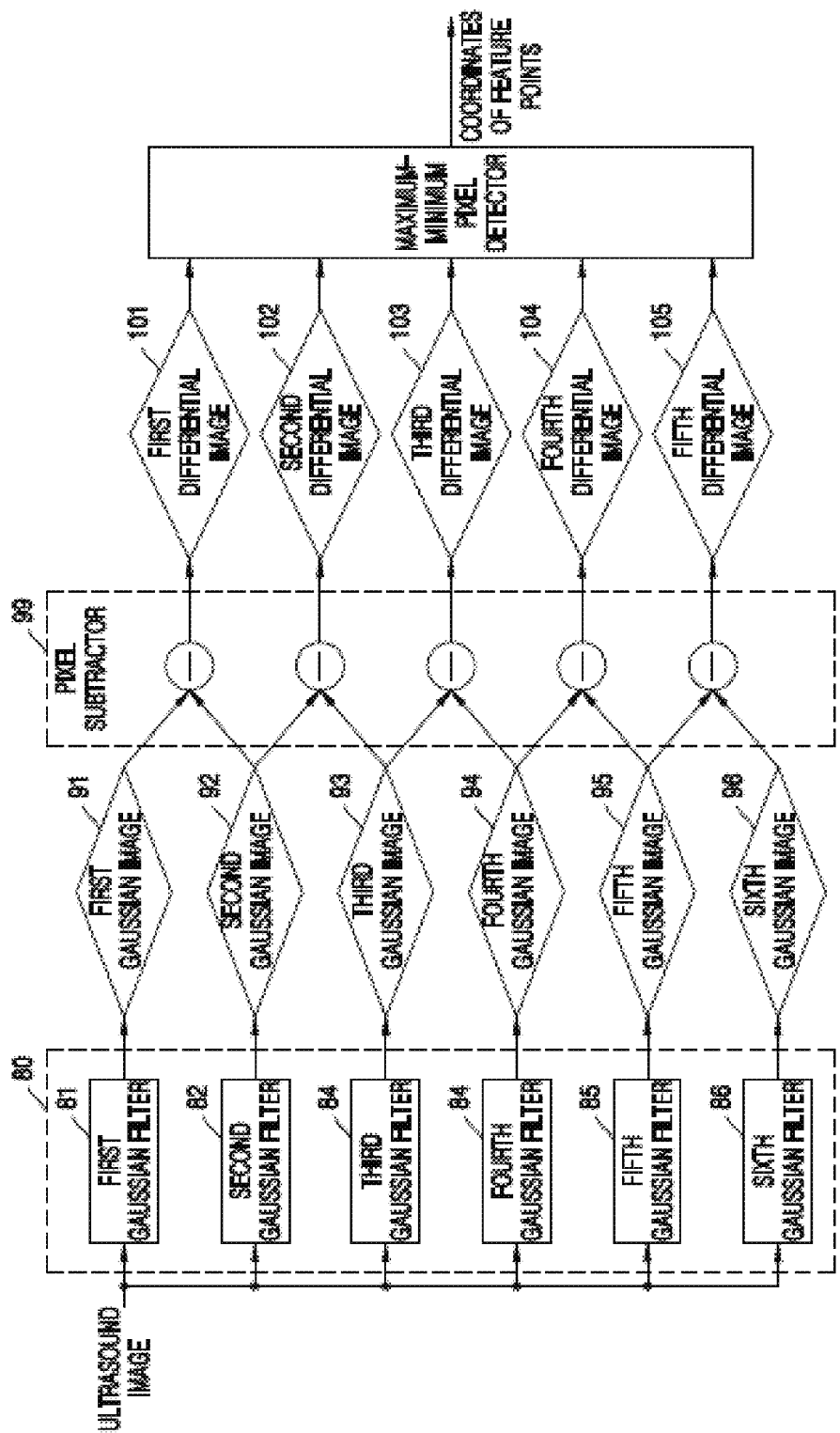

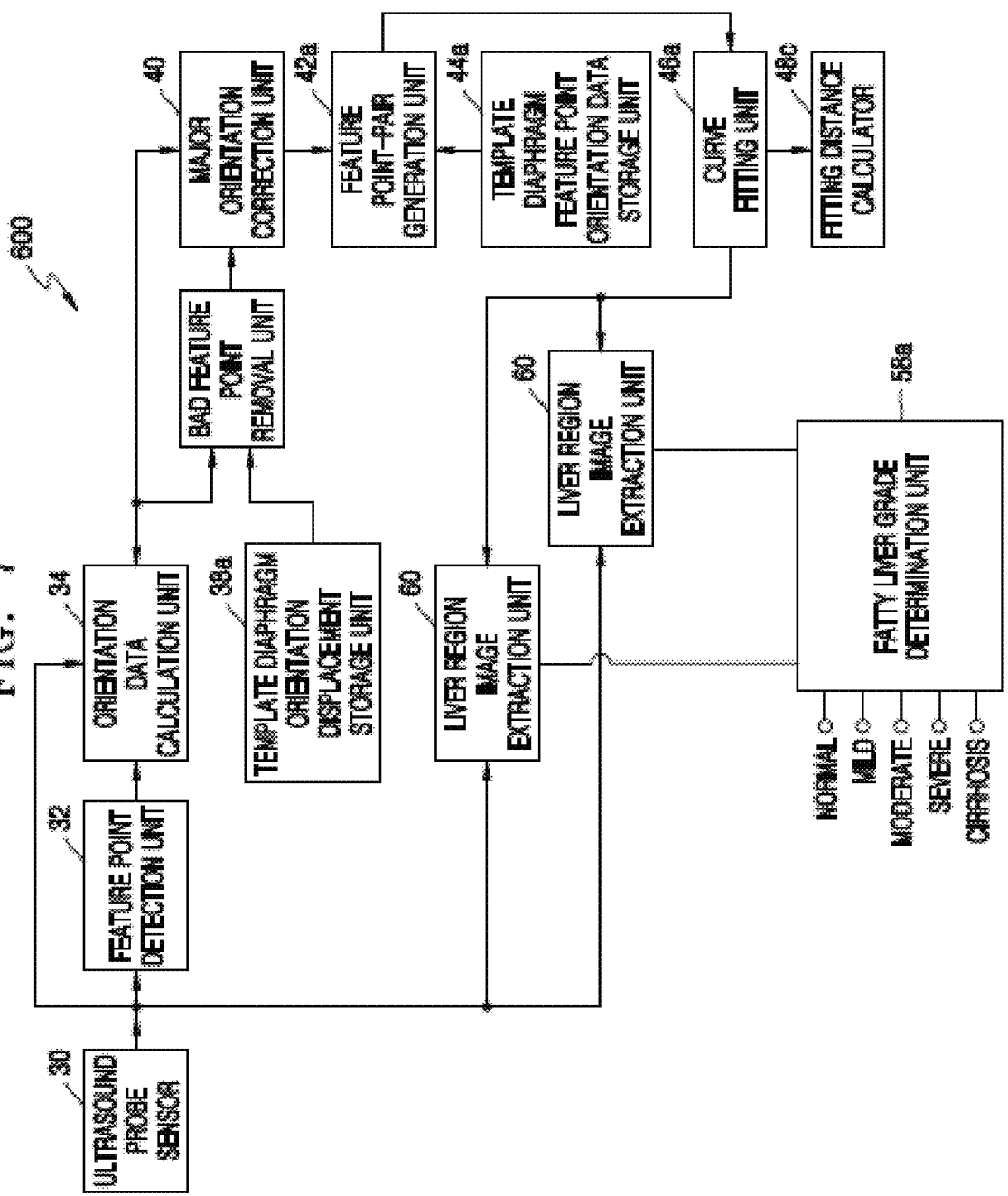

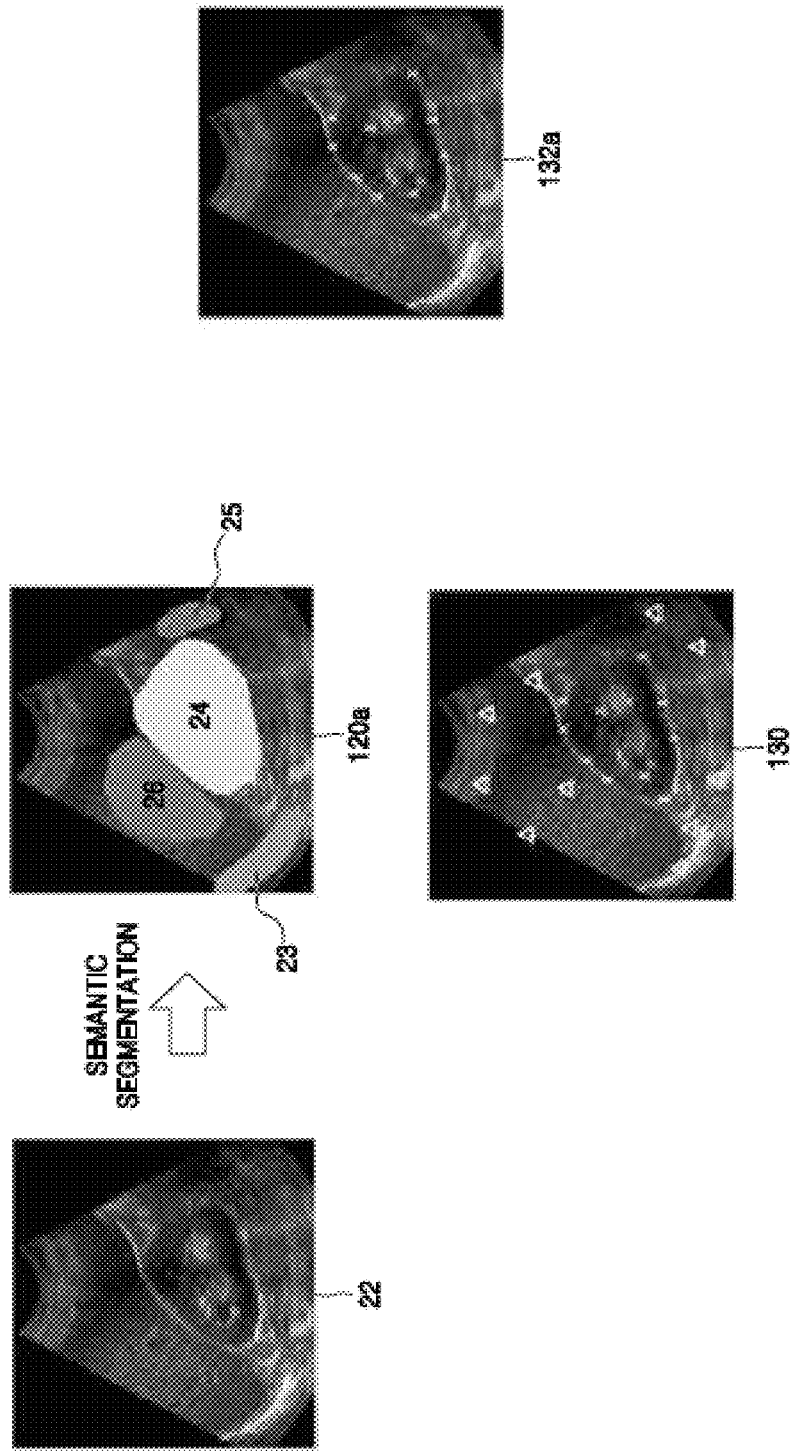

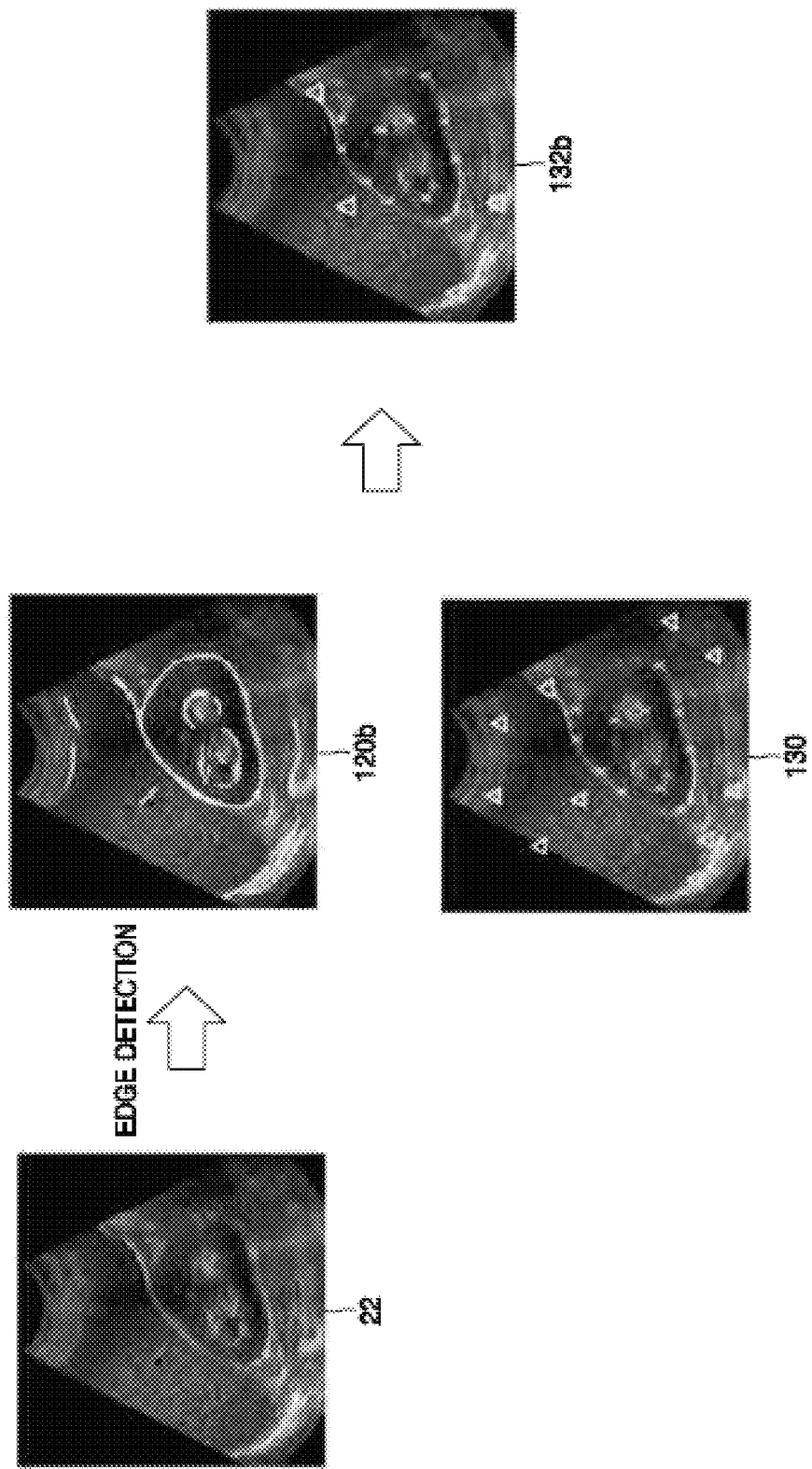

APPARATUS FOR ULTRASOUND DIAGNOSIS OF LIVER STEATOSIS USING FEATURE POINTS OF ULTRASOUND IMAGE AND REMOTE MEDICAL-DIAGNOSIS METHOD USING THE SAME

CROSS-REFERENCE TO RELATED APPLICATION

This application claims the benefit of and priority to Korean Patent Application 10-2019-0092089, filed on Jul. 30, 2019 in the Korean Intellectual Property Office, the entire disclosure of which is incorporated herein by reference.

FIELD

The present invention relates to an apparatus for automatic ultrasound diagnosis of liver steatosis using feature points in an ultrasound image, which can automatically determine a grade of liver steatosis, which is difficult to determine visually, through extraction from an image acquired by medical imaging, and a remote medical diagnosis method using the same. More particularly, the present invention relates to an apparatus for automatic ultrasound diagnosis of liver steatosis using feature points in an ultrasound image, which includes a fatty liver grade determination unit adapted to locate feature points in an ultrasound image, remove bad feature points from the located feature points, determine candidate locations of the kidney in the ultrasound image by comparing the feature points, from which the bad feature points are removed, with feature points of template kidney ultrasound images, and determine the grade of liver steatosis based on similarity between the feature points of the template kidney ultrasound images and the feature points at the candidate locations of the kidney in the ultrasound image, thereby achieving automatic determination of the grade of liver steatosis of a patient based on ultrasound images of the patient input from an ultrasound image sensor, and a remote medical diagnosis method using the same.

In addition, the present invention is advantageously used in implementation of a virtual doctor that automatically analyzes the grade of liver steatosis of a patient using the apparatus for automatic ultrasound diagnosis of liver steatosis, notifies the patient or a doctor of an analysis result, and provides a remote consultation service via the Internet.

BACKGROUND

This application is a continuation of an earlier-issued European patent titled "Remote Medical-Diagnosis System and Method" (issued on Dec. 12, 2018, Patent No. 02140412).

The above patent discloses a remote medical diagnosis system and a remote medical diagnosis method using the same, the remote medical diagnosis system including: a bioanalyzer including a bio-disc or a lab-on-a-disc adapted to receive a sample therein to perform a biological, chemical or biochemical reaction; a virtual doctor including a medical examination device including a thermometer, a sphygmomanometer, a camera, a stethoscope, a body fat analyzer, a vascular screening device, an ultrasound imager, a urinalysis device, a pulsimeter, a blood collection device, an electrocardiographer, an X-ray device, an oxygen saturation tester, a dementia testing device, a computerized axial tomographer (CAT), a magnetic resonance imager (MRI), a capsule endoscope, a magnifier, a camera-integrated magnifier, and a bioshirt having a function of measuring biological signals (diabetes, obesity, blood pressure, pulse, electrocardiogram, body temperature, and the like), the virtual doctor residing as software in a user terminal to guide or instruct how to use the bioanalyzer and the medical examination device and provide a consultation service with a user; a user terminal providing a consultation service with a medical expert or the virtual doctor; a medical expert terminal providing a consultation service with a user; and a remote diagnosis server connecting a user to a medical expert as a consultation specialist during a regular medical check-up period, connecting a user to the virtual doctor during the other periods, and blocking connection between the user and the virtual doctor if the regular medical check-up period elapses without consultation with the medical expert.

Recently, as digital image processing technology has been used in the field of clinical diagnosis along with medical device manufacturing technology, there have been many advances in diagnostic radiology.

In particular, ultrasound diagnosis is thus harmless to the human body by allowing avoidance of exposure to harmful radiation, as compared with CT or X-ray medical equipment, allows acquisition of a cross-sectional image of the human body in a non-invasive manner, and is portable and inexpensive. Particularly, ultrasound diagnosis allows real-time image acquisition and thus real-time observation of movement of an organ.

Such an ultrasound diagnostic technique is widely used to determine the grade of liver steatosis using the fact that reflection properties of ultrasound waves significantly differ between water and fat.

Fatty liver is the most common disease and is detected by abdominal ultrasonography. Recently, diagnosis of liver steatosis is mainly carried out by measuring the brightness level or texture properties of an abdominal cross-sectional image obtained by ultrasound equipment and calculating a hepatorenal sonographic index (HI), which is a measure for determining the degree of steatosis in liver tissue, wherein the HI is generally a ratio of mean brightness level or degree of texture between a liver and a right kidney on an echogenicity histogram of a cortex. However, diagnosis of fatty liver based on the hepatorenal sonographic index (HI) obtained using the brightness level or the texture characteristics of an ultrasound image has a problem in that calculation errors are likely to occur due to low resolution of the ultrasound image and severe noise. In addition, the ultrasound image is often severely damaged, causing difficulty in accurate medical interpretation by nonprofessionals. Further, fatty liver is divided into four grades: normal, mild, moderate, and severe, and, in more severe cases, may be diagnosed as liver cirrhosis or liver cancer.

Inaccuracy of calculation of the HI leads to increase in ambiguity of determination of the fatty liver grade using ultrasound examination and, eventually, the determination depends on subjective judgment of an examiner, causing inconsistency between opinions of different examiners and confusion in reading results of ultrasound examination. In addition, although it is necessary to determine the location of the liver for diagnosis of fatty liver, it is difficult to determine the location of the liver in an ultrasound image due to low resolution and severe noise and liver steatosis is determined through calculation of the HI after determination of the location of the liver through manual operation of an experienced doctor.

The present invention has been conceived to solve such problems in the art and provides an apparatus for automatic ultrasound diagnosis of liver steatosis using feature points in an ultrasound image, which includes a fatty liver grade determination unit adapted to locate feature points in an ultrasound image, remove bad feature points from the located feature points, obtain candidate locations of the kidney in the ultrasound image by comparing the feature points, from which the bad feature points are removed, with feature points of template kidney ultrasound images, and determine the grade of liver steatosis based on similarity between the feature points of the template kidney ultrasound images and the feature points at the candidate locations of the kidney in the ultrasound image, thereby achieving automatic determination of the grade of liver steatosis of a patient based on ultrasound images of the patient input from an ultrasound image sensor, and a remote medical diagnosis method using the same.

SUMMARY

The present invention has been conceived to solve such problems in the art and it is one aspect of the present invention to provide an apparatus for automatic ultrasound diagnosis of liver steatosis using feature points in an ultrasound image, which includes a fatty liver grade determination unit adapted to locate feature points in an ultrasound image, remove bad feature points from the located feature points, obtain candidate locations of the kidney in the ultrasound image by comparing the resulting feature points with feature points of template kidney ultrasound images, and determine the grade of liver steatosis based on similarity between the feature points of the template kidney ultrasound images and the feature points at the candidate locations of the kidney in the ultrasound image in order to diagnose liver steatosis of a patient from an ultrasound image, thereby achieving automatic determination of the grade of liver steatosis of a patient based on ultrasound images of the patient input from an ultrasound image sensor, and a remote medical diagnosis method using the same.

It is another aspect of the present invention to provide a remote medical diagnosis method which automatically analyzes the grade of liver steatosis in a patient using the apparatus for automatic ultrasound diagnosis of liver steatosis set forth above, notifies the patient or a doctor of an analysis result via the Internet, and provides a consultation service with a medical expert using a virtual doctor.

However, it should be understood that the technical problem to be solved by embodiments of the present invention is not limited to the aforementioned technical problems and other technical problems may exist.

In accordance with one aspect of the present invention, an apparatus for automatic ultrasound diagnosis of liver steatosis using feature points in an ultrasound image includes: an ultrasound probe sensor acquiring an ultrasound image from a patient; a template kidney feature point orientation data storage unit storing orientation data with respect to template kidney periphery feature points corresponding to feature points of a kidney periphery in template ultrasound pictures and pixels in a patch image of each of the feature points; a feature point detection unit detecting feature points from the ultrasound image or from an edge component of the ultrasound image; an orientation data calculation unit calculating orientation data with respect to pixels in a patch image of each of the feature points of the ultrasound image; a bad feature point removal unit including an edge detector adapted to detect the edge component of the ultrasound image and an edge feature point overlapping determiner adapted to determine whether the edge component overlaps the feature points of the ultrasound image on two-dimensional ultrasound image space coordinates to locate feature points for comparison through removal of bad feature points from the feature points of the ultrasound image, the bad feature points being determined by considering feature points of the ultrasound image not overlapping the edge component to be the bad feature points; a major orientation correction unit obtaining the most frequent orientation as a major rotational orientation in a histogram indicating the frequency of pixels with respect to an orientation, based on orientation data with respect to pixels in a patch image of each of the feature points for comparison, and correcting orientations of the pixels in the patch image of each of the feature points for comparison based on the major rotational orientation; a feature point-pair generation unit generating a pair of feature points between the template kidney periphery feature points and the feature points for comparison pertaining to patch images having high similarity through comparison between the orientation data with respect to the pixels in the patch images of the template kidney periphery feature points and in the patch images of the feature points for comparison; a curve fitting unit generating a first fitting curve through ellipse fitting or curve fitting with respect to an imaginary closed loop formed by connecting the feature points for comparison paired with the template kidney periphery feature points by the feature point-pair generation unit, or calculating the number of fitting feature points corresponding to the number of feature points overlapping each other on two-dimensional space coordinates through scanning comparison between a template edge component and the feature points for comparison paired with the template kidney periphery feature points by the feature point-pair generation unit; a kidney detection unit detecting a location of the kidney from the ultrasound image based on the first fitting curve or the number of fitting feature points; a region-of-interest extraction unit extracting images of one or more regions of interest through space addressing on the ultrasound image with reference to the detected kidney (location of the kidney); an image integration unit concatenating images of the regions of interest in the template ultrasound pictures or in the ultrasound image into one integrated image; and an artificial neural network trained on the integrated image by deep learning, wherein the deep learning-trained artificial neural network is used to automatically determine the grade of liver steatosis of the patient based on the integrated image obtained from the ultrasound image of the patient input from the ultrasound probe sensor.

An ultrasound image of a person having an abnormal fatty liver grade is much cloudier than an ultrasound image of a person having a normal fatty liver grade or is generally white. However, there is substantially no difference between images of kidney regions thereof.

As such, since image patterns between an integrated image of a person having a normal fatty liver grade and an integrated image of a person having an abnormal fatty liver grade are significantly different, it is possible to achieve efficient learning and recognition through an artificial neutral network.

Herein, a template edge refers to an edge component comprising all of feature points of a kidney periphery in a template ultrasound picture.

The width of the template edge may be set to be greater than an actual edge width in consideration of various changes of an ultrasound image (variation possibility), that is, diversity thereof.

Herein, the number of fitting feature points refers to the number of feature points overlapping each other on two-dimensional space coordinates and calculated through scanning comparison between the template edge component and the feature points for comparison (final feature points) paired with the template kidney periphery feature points by the feature point-pair generation unit.

The bad feature point removal unit serves to reduce burden in calculation of the feature point-pair generation unit through previous removal of the bad feature points from many ultrasound images in the process of preparing the feature points for comparison.

In the present invention, among the feature points for comparison, feature points paired with the template kidney periphery feature points by the feature point-pair generation unit are referred to as "final feature points".

The kidney detection unit may include: a fitting distance calculator calculating, as a fitting distance, a Euclidean distance between the first fitting curve and the feature points for comparison applied to fitting; and a fitting similarity determiner determining similarity to the fitting curve based on the fitting distance. Upon determining that fitting similarity between the first fitting curve and the feature points for comparison applied to fitting is high or that a diameter of the first fitting curve, lengths of a major axis and a minor axis or the shape of the fitting curve is similar to the template kidney periphery, it can be determined that a kidney is present in the ultrasound image.

Alternatively, the kidney detection unit may include: a fitting distance calculator calculating, as a fitting distance, a Euclidean distance between the first fitting curve and a second fitting curve obtained by curve fitting with respect to an imaginary closed loop formed by connecting the template kidney periphery feature points; and a fitting similarity determiner determining similarity between the first fitting curve and the second fitting curve based on the fitting distance.

Here, a closed loop shape formed by the second fitting curve will be referred to as Object A2 and a closed loop shape formed by the first fitting curve will be referred to as Object A1.

The Euclidean distance between the second fitting curve and the first fitting curve may be calculated by aligning the second fitting curve with the first fitting curve at a location where a correlation coefficient between Object A1 and Object A2 reaches a maximum value, followed by obtaining a distance difference between these two curves while rotating the first fitting curve about the center of gravity of the second fitting curve by 360 degrees.

Alternatively, the Euclidean distance between the second fitting curve and the first fitting curve may be calculated by aligning the second fitting curve with the first fitting curve such that the center of gravity of Object A1 is coincident with the center of gravity of Object A2, followed by obtaining a distance difference between these two curves while rotating the first fitting curve about the center of gravity of the second fitting curve by 360°.

The kidney detection unit may calculating the number of fitting feature points overlapping each other through scanning comparison between the template edge component and the feature points for comparison paired with the template kidney periphery feature points by the feature point-pair generation unit on the two-dimensional space coordinates, and may determine that a kidney is present at a coordinate location at which the number of fitting feature points is a predetermined number or more and reaches the maximum value.

The orientation data stored in the template kidney feature point orientation data storage unit may be corrected such that the major rotational orientation becomes 0 degrees.

After correction of the orientations of the pixels in the patch image of each of the feature point for comparison by the major orientation correction unit, a major orientation of the patch image of the feature point for comparison may become 0 degrees.

The sum of Euclidean distances between the first fitting curve and the feature points for comparison applied to generation of the first fitting curve or the sum of Euclidean distances between the first fitting curve and the second fitting curve may be used in determination of fitting similarity.

A lower sum of the Euclidean distances may indicate higher fitting similarity.

Curve fitting may be performed by a curve fitting technique or a random sample consensus technique, which is known in the art.

In the present invention, extraction of the edge component is a process of detecting a contour line or a boundary line of an object in an image, and the intensity of the image abruptly changes in the contour line or the boundary line of the image. A portion in which the intensity of the image abruptly changes is referred to as an edge or a periphery. In the present invention, detection of the edge component may be performed by any one of Sobel, Prewitt, Laplacian, Roberts, and Kenny edge detection techniques.

If the Euclidean distance calculated by the fitting distance calculator is greater than a predetermined value, it can be determined that there is no kidney region image in the ultrasound image.

In the present invention, determination of the fitting similarity or the orientation data similarity may be performed by any one of SSD (sum of squared difference (SSD), sum of absolute difference (SAD), K-nearest neighbors (KNN), and normalized cross correlation (NCC).

In the present invention, the template ultrasound pictures may be composed of ultrasound pictures of normal humans free from disease around the kidneys and the liver.

In accordance with another aspect of the present invention, an apparatus for automatic ultrasound diagnosis of liver steatosis using feature points in an ultrasound image includes: an ultrasound probe sensor acquiring an ultrasound image from a patient; a template kidney feature point orientation data storage unit storing orientation data with respect to template kidney periphery feature points corresponding to feature points of a kidney periphery in template ultrasound pictures and pixels in a patch image of each of the feature points; a template feature point statistical data storage unit storing statistical data with respect to feature points of a kidney region in the template ultrasound pictures and feature points of regions of interest excluding the kidney region; a feature point detection unit detecting feature points from the ultrasound image or from an edge component of the ultrasound image; an orientation data calculation unit calculating orientation data with respect to pixels in a patch image of each of the feature points of the ultrasound image; a bad feature point removal unit including an edge detector adapted to detect the edge component of the ultrasound image and an edge feature point overlapping determiner adapted to determine whether the edge component overlaps the feature points of the ultrasound image on two-dimensional ultrasound image space coordinates to locate feature points for comparison through removal of bad feature points from the feature points of the ultrasound image, the bad feature points being determined by considering feature points of the ultrasound image not overlapping the edge components to be the bad feature points; a major orientation correction unit obtaining the most frequent orientation as a major rotational orientation in a histogram indicating the frequency of pixels with respect to an orientation, based on orientation data with respect to pixels in a patch image of each of the feature points for comparison, and correcting orientations of the pixels in the patch image of each of the feature points for comparison based on the major rotational orientation; a feature point-pair generation unit generating a pair of feature points between the template kidney periphery feature points and the feature points for comparison pertaining to patch images having high similarity through comparison between the orientation data with respect to the pixels in the patch images of the template kidney periphery feature points and in the patch images of the feature points for comparison; a curve fitting unit generating a first fitting curve through ellipse fitting or curve fitting with respect to an imaginary closed loop formed by connecting the feature points for comparison paired with the template kidney periphery feature points, or calculating the number of fitting feature points corresponding to the number of feature points overlapping each other on two-dimensional space coordinates through scanning comparison between a template edge component and the feature points for comparison paired with the template kidney periphery feature points by the feature point-pair generation unit; a kidney detection unit detecting a location of the kidney from the ultrasound image based on the first fitting curve or the number of fitting feature points; a region-of-interest extraction unit extracting images of one or more regions of interest through space addressing on the ultrasound image with reference to the detected kidney (location of the kidney); a feature point statistical data calculation unit calculating feature point statistical data from the feature points of the kidney region detected by the kidney detection unit or from the feature points of the regions of interest extracted by the region-of-interest extraction unit; and a fatty liver grade determination unit determining a grade of liver steatosis classified into a mild grade, a moderate grade, a severe grade, and a cirrhosis grade, based on the template feature point statistical data and the feature point statistical data obtained (acquired) from the feature point statistical data calculation unit, thereby achieving automatic determination of the grade of liver steatosis of the patient based on ultrasound images of the patient input from the ultrasound image sensor.

The edge detector may further include an edge width expander adapted to generate an edge component having an expanded width through expansion of a width of the edge component detected by the edge detector in a two-dimensional space.

When the edge component having an expanded width is used instead of an actual edge component, it is possible to prevent feature points immediately adjacent to the actual edge component from being considered to be the bad feature points.

Herein, a small image obtained by collecting pixels around a feature point in the ultrasound image is referred to as the patch image. In addition, a patch image formed from a feature point for comparison is referred to as the patch image for comparison.

In the present invention, the patch image may be any one image selected from the group of, for example, a first sub-patch image, a second sub-patch image, and a third sub-patch image.

The first sub-patch image may be composed of, for example, 16×16 pixels around a feature point.

The second sub-patch image may be composed of, for example, four images each composed of 8×8 pixels, as obtained by quartering an image composed of 16×16 pixels around a feature point.

The third sub-patch image may be composed of, for example, sixteen images each composed of 4×4 pixels, as obtained by dividing an image composed of 16×16 pixels around a feature point into 16 equal parts.

The feature point statistical data may include at least some selected from the group of the number of feature points included in a certain region designated in the ultrasound image, the number of fitting feature points, a histogram indicating intensity distribution of the feature points, an orientation displacement of the feature points, an average of the orientation data of the feature points, a distribution of the orientation data of the feature points, and a standard deviation of the orientation data of the feature points.

The orientation displacement of the feature points means an orientation difference between the maximum orientation and the minimum orientation among candidate orientations having the maximum magnitudes and obtained from patch images of each of the feature points.

The fatty liver grade determination unit may determine the grade of liver steatosis through calculation of a ratio of statistical data included in a kidney cortex or kidney periphery region corresponding to the kidney in the ultrasound image of the patient to statistical data included in a non-kidney region of the ultrasound image.

For example, when the average of the orientation data is used as the statistical data, a ratio of an average value of orientations of the feature points in the kidney region to an average value of orientations of the feature points in the non-kidney region may be used. For example, since a person having a normal fatty liver grade has a lower ratio than a person having a severe fatty liver grade, this ratio may be used in determination of the fatty liver grade.

The fatty liver grade determination unit may determine the grade of liver steatosis through calculation of a ratio of the number of feature points included in the kidney cortex or kidney periphery region corresponding to the kidney in the ultrasound image of the patient to the number of feature points included in the non-kidney region of the ultrasound image. That is, the fatty liver grade may be determined by calculating the ratio of the number of kidney feature points to the number of non-kidney feature points.

For example, when an ultrasound image of a patient having a normal grade fatty liver is used as the template ultrasound picture, it is apparent that a higher fatty liver grade provides a higher ratio of the number of kidney feature points to the number of non-kidney feature points due to a significant increase or decrease in the number of feature points in the non-kidney region.

That is, the fatty liver grade of the patient may be determined by calculating the ratio of the number of kidney feature points to the number of non-kidney feature points and gradually increasing the grade of liver steatosis to, for example, a mild grade, a moderate grade, and a severe grade, with increasing difference between the ultrasound image of the patient and the template ultrasound picture in terms of the ratio of the number of kidney feature points to the number of non-kidney feature points.

The non-kidney region may be extracted by the region-of-interest extraction unit.

The apparatus for automatic ultrasound diagnosis of liver steatosis may further include a template region-of-interest orientation displacement storage unit obtaining candidate orientations having the maximum magnitudes from each of patch images of the feature points of the regions of interest in the template ultrasound pictures having a normal grade of liver steatosis and storing orientation displacement data corresponding to an orientation difference between the maximum orientation and the minimum orientation among the candidate orientations, and the fatty liver grade determination unit may detect the feature points of the regions of interest in the ultrasound image of the patient and determine the grade of liver steatosis based on the number of fatty liver feature points corresponding to feature points, which are included in the regions of interest of the ultrasound image of the patient and deviate from the range of the orientation displacement stored in the template region-of-interest orientation displacement storage unit.

It is apparent that a higher fatty liver grade provides a more significant variation in the number of fatty liver feature points in a region of interest than a normal grade ultrasound image.

The apparatus for automatic ultrasound diagnosis of liver steatosis may further include a template liver orientation displacement storage unit obtaining candidate orientations having the maximum magnitudes from each of patch images of feature points of a liver region in the template ultrasound pictures having a normal grade of liver steatosis and storing orientation displacement data corresponding to an orientation difference between the maximum orientation and the minimum orientation among the candidate orientations, and the fatty liver grade determination unit may detect the feature points of the liver region in the ultrasound image of the patient and determine the grade of liver steatosis based on the number of fatty liver feature points corresponding to the feature points, which are included in the liver region of the ultrasound image of the patient and deviate from the range of the orientation displacement stored in the template liver orientation displacement storage unit.

The feature point detection unit may include: a Gaussian filter unit including Gaussian filter 1 composed of Standard deviation 1 generating a first Gaussian image from the ultrasound image, a second Gaussian filter composed of Standard deviation 2 generating a second Gaussian image and having a greater value than Standard deviation 1, a third Gaussian filter composed of Standard deviation 3 generating a third Gaussian image and having a greater value than Standard deviation 2, a fourth Gaussian filter composed of Standard deviation 4 generating a fourth Gaussian image and having a greater value than Standard deviation 3, a fifth Gaussian filter composed of Standard deviation 5 generating a fifth Gaussian image and having a greater value than Standard deviation 4, and a sixth Gaussian filter composed of Standard deviation 6 generating a sixth Gaussian image and having a greater value than Standard deviation 5; a pixel subtractor performing subtraction for each pixel between the first Gaussian image and the second Gaussian image to obtain a first differential image, performing subtraction for each pixel between the second Gaussian image and the third Gaussian image to obtain a second differential image, performing subtraction for each pixel between the third Gaussian image and the fourth Gaussian image to obtain a third differential image, performing subtraction for each pixel between the fourth Gaussian image and the fifth Gaussian image to obtain a fourth differential image, and performing subtraction for each pixel between the fifth Gaussian image and the sixth Gaussian image to obtain a fifth differential image; and a maximum-minimum pixel detector generating a first scan window, a second scan window, and a third scan window each having a size of 3×3 for scanning through parallel synchronization of the second differential image together with the differential images (first differential image and third differential image) adjacent thereto, determining whether a pixel value of central coordinates of the second scan window is the maximum value or the minimum value among all pixel values (26 pixels) in the first to third scan windows, and determining that a feature point of the pixel value is an effective feature point if the pixel value is greater than or equal to a feature point determination reference value, in order to determine the feature points in the ultrasound image.

The Gaussian filter $G(x, y, \sigma)$ with respect to the two-dimensional space coordinates $(x, y)$ is calculated by the following equation and is a function of standard deviation $(\sigma)$.

$$G(x, y, \sigma) = \frac{1}{2\pi\sigma^2} e^{-(x^2+y^2)/2\sigma^2}$$

Since the second Gaussian image employs a Gaussian filter having a greater standard deviation than the first Gaussian image, the second Gaussian image is more unclear than the first Gaussian image.

Herein, the orientation data calculation unit may calculate orientation data with respect to a certain feature point and the orientation data is defined as a set $\{m(x, y), \theta(x, y)\}$ of Gradient directions $\theta(x, y)$ and magnitudes $m(x, y)$ calculated from pixels in a patch image and is calculated by the following equation.

<Equation>

$$m(x, y) = \sqrt{(L(x+1,y)-L(x-1,y))^2+(L(x,y+1)-L(x,y-1))^2}$$

$$\theta(x, y) = \tan^{-1}((L(x, y+1)-L(x, y-1))/(L(x+1, y)-L(x-1, y)))$$

In this equation, $L(x, y)$ may indicate the intensity of a pixel on a Gaussian image at the pixel coordinates $(x, y)$ in a patch image.

The magnitude component of the Gradient direction $\theta(x, y)$ is determined by the magnitude at the corresponding coordinates $(x, y)$.

For calculation of the orientation data $\{m(x, y), \theta(x, y)\}$ of the feature points, the orientation data calculation unit may constitute a first sub-patch image composed of 16×16 pixels around each of the feature points, four second sub-patch images each composed of 8×8 pixels and obtained by quartering the first sub-patch image, and sixteen third sub-patch images each composed of 4×4 pixels and obtained by dividing the first sub-patch image into 16 equal parts.

For all pixels in each of the sub-patch images, the Gradient directions $\theta(x, y)$ and the magnitudes $m(x, y)$ may be calculated using the above equation, and the set $\{m(x, y), \theta(x, y)\}$ obtained by adding up the magnitudes $m(x, y)$ of pixels having similar Gradient directions $\theta(x, y)$ in each of the sub-patch images may be used as orientation data of the corresponding sub-patch.

The similar Gradient directions $\theta(x, y)$ may be assigned at intervals of 45 degrees. For example, the similar Gradient directions $\theta(x, y)$ may be assigned in eight orientation zones, such as $0° \leq \theta \leq 44°$, $45° \leq \theta \leq 89°$, . . . , and $315° \leq \theta \leq 359°$. That is, the Gradient directions $\theta(x, y)$ in a zone of $0° \leq \theta \leq 44°$ may be considered to have similar Gradient directions $\theta(x, y)$.

As such, since one sub-patch image is divided into eight orientation zones, one sub-patch image includes 8 orientation data.

If the second sub-patch image is used for calculation of the orientation data, each feature point includes a total of 32 orientation data since each feature point includes 4 second sub-patch images.

If the third sub-patch image is used for calculation of the orientation data, each feature point includes a total of 128 orientation data since each feature point includes 16 third sub-patch images.

In the present invention, the major orientation data includes orientation data with respect to 256 pixels included in the first sub-patch image and the most frequent orientation in a histogram showing accumulation of magnitudes m(x, y) of the 256 pixels with respect to an orientation θ(x, y) is defined as a major rotational orientation.

The histogram for obtaining the major rotational orientation may be obtained by dividing the Gradient directions θ(x, y) at intervals of 10 degrees (10°).

In the present invention, correction of the major orientation is obtained by subtracting the major rotational orientation from θ(x, y).

The orientation displacement data may be defined as a difference between the maximum orientation and the minimum orientation among candidate orientations obtained by the Gradient directions of pixels having the maximum magnitudes from each of the patch images.

For example, assuming that the number of patch images is 5, and, in calculation of the Gradient directions θ(x, y) and the magnitudes m(x, y) of pixels in each of the patch images, the Gradient direction having the maximum magnitude m(x, y) with respect to the first patch image is denoted by $θ_1$, the Gradient direction having the maximum magnitude m(x, y) with respect to the second patch image is denoted by $θ_2$, the Gradient direction having the maximum magnitude m(x, y) with respect to the third patch image is denoted by $θ_3$, the Gradient direction having the maximum magnitude m(x, y) with respect to the fourth patch image is denoted by $θ_4$, and the Gradient direction having the maximum magnitude m(x, y) with respect to the fifth patch image is denoted by $θ_5$.

Here, $θ_1$, $θ_2$, $θ_3$, $θ_4$ and $θ_5$ are referred to as the candidate orientations.

Among these candidate orientations $θ_1$, $θ_2$, $θ_3$, $θ_4$ and $θ_5$, a difference between the maximum orientation and the minimum orientations is defined as the orientation displacement data.

Maximum orientation=max($θ_1$, $θ_2$, $θ_3$, $θ_4$, $θ_5$)

Minimum orientation=min($θ_1$, $θ_2$, $θ_3$, $θ_4$, $θ_5$)

Orientation displacement data=Maximum orientation−Minimum orientation

For example, if the template ultrasound picture has 10 feature points and the third sub-patch image is used, 160 candidate orientations are generated since each of the feature point has 16 patch images, and a difference between the maximum orientation and the minimum orientation among the candidate orientations is provided as displacement data.

Calculation of the candidate orientation may be performed using the third sub-patch image or any one of the second sub-patch image and the first sub-patch image.

The region of interest may be at least one image region selected from the group of an image of a liver cortex region, an image of a kidney cortex region, an image of a right portal vein (RPV) region, an image of a hepatic vein region, an image of a spleen region, an image of a diaphragm region, an image of a kidney renal pelvis region, and an image of a kidney renal sinus region.

The template ultrasound pictures and the template kidney ultrasound pictures may be ultrasound pictures of a normal fatty liver grade.

The grade of liver steatosis may be any one of a mild grade, a normal grade, a moderate grade, a severe grade, and a cirrhosis grade.

The fatty liver grade determination unit may employ a support vector machine (SVM). In this case, the feature point statistical data may be used as a feature vector for classification of the grade of liver steatosis.

The artificial neutral network may be a convolutional neural network (CNN) or a recurrent neural network (RNN).

The artificial neural network is a neural network allowing deep learning and may be constituted by combination of one or more layers or elements selected from the group of a convolution layer, a pooling layer, an ReLu layer, a transpose convolution layer, an unpooling layer, a 1×1 convolution layer, a skip connection layer, a global average pooling (GAP) layer, a fully connected layer, a support vector machine (SVM), and a long short term memory (LSTM). The artificial neutral network may further include a calculator for batch normalization calculation at a front end of the ReLu layer.

The ultrasound image may be an ultrasound image of a parasagittal scan plane allowing easy observation of organs, such as the liver, the right portal vein (RPV), the hepatic vein, the kidney, the spleen, and the diaphragm.

In accordance with a further aspect of the present invention, an apparatus for automatic ultrasound diagnosis of liver steatosis using feature points in an ultrasound image includes: an ultrasound probe sensor acquiring an ultrasound image from a patient; a template diaphragm feature point orientation data storage unit storing orientation data with respect to template diaphragm feature points corresponding to feature points of the diaphragm included in template ultrasound pictures and pixels in a patch image of each of the feature points; a template diaphragm orientation displacement storage unit obtaining candidate orientations having the maximum magnitudes from each of the patch images corresponding to the template diaphragm feature points and storing orientation displacement data corresponding to a difference between the maximum orientation and the minimum orientation among the candidate orientations; a feature point detection unit detecting feature points in the ultrasound image; an orientation data calculation unit calculating orientation data with respect to pixels in a patch image of each of the feature points of the ultrasound image; a bad feature point removal unit removing bad feature points from the feature points obtained from the ultrasound image to locate feature points for comparison, the bad feature points being determined by considering feature points of the ultrasound image including a predetermined ratio or more of pixels in a patch image deviating from a template diaphragm orientation displacement range to be the bad feature points; a major orientation correction unit obtaining the most frequent orientation as a major rotational orientation in a histogram indicating the frequency of pixels with respect to an orientation, based on orientation data with respect to pixels in a patch image of each of the feature points for comparison from the patch image of each of the feature points for comparison, and correcting orientations of the pixels in the patch image of each of the feature points for comparison such that the major rotational orientation becomes 0 degrees; a feature point-pair generation unit generating a pair of feature points between the feature points using patch images having high similarity through comparison between the orientation data with respect to the pixels in the patch images of the template diaphragm feature points and in the patch images of the feature points for comparison; a curve fitting unit generating a two-dimensional curve fitting curve through curve fitting with respect to an imaginary closed loop formed by connecting the feature points for comparison paired with the template diaphragm feature points; a diaphragm image extraction unit extracting an image of a diaphragm region from the two-dimensional curve fitting curve; a fitting distance calculator calculating a Euclidean distance between the two-dimensional curve fitting curve and the feature points for comparison applied to curve fitting; a region-of-interest image extraction unit extracting an image of a region of interest from the ultrasound image through detection of a location of the region of interest based on a location of the extracted image of the diaphragm region; and a fatty liver grade determination unit determining a grade of liver steatosis classified into a mild grade, a moderate grade, a severe grade, and a cirrhosis grade, based on a "brightness ratio of the region of interest to the diaphragm region" obtained by calculating an average brightness of pixels in the extracted image of the region of interest and an average brightness of pixels in the extracted image of the diaphragm region, wherein the grade of liver steatosis of the patient is automatically determined based on the "brightness ratio of the region of interest to the diaphragm region" obtained from the ultrasound image of the patient input from the ultrasound probe sensor.

For example, when a liver region is provided as the region of interest, the brightness ratio of the liver region to the diaphragm region can increase, since the liver having a severe grade of liver steatosis generally has a much higher brightness in the pixels of the liver region than the liver having a mild grade of liver steatosis.

If the Euclidean distance calculated by the fitting distance calculator is greater than a predetermined value, it can be determined that there is no image of the diaphragm region in the ultrasound image.

In addition, for determination of the grade of liver steatosis, a brightness ratio of the kidney region to the diaphragm region may be used instead of the brightness ratio of the liver region to the diaphragm region.

The bad feature point removal unit may include an artificial neural network performing semantic segmentation to detect the location of the kidney from the ultrasound image, and may acquire the feature points for comparison by training the artificial neural network on template kidney images, detecting a kidney region through semantic segmentation of the ultrasound image of the patient input from the ultrasound probe sensor, and removing the bad feature points from feature points obtained from the ultrasound image of the patient by the feature point detection unit, in which the bad feature points are acquired by considering the feature points of the ultrasound image excluding feature points in the kidney region detected through semantic segmentation to be the bad feature points.

When the kidney is observed in the ultrasound image, the semantic segmentation may be performed by the artificial neural network segmenting the kidney in pixel units to determine a location of the kidney in the ultrasound image and separating the kidney region from other objects.

Curve fitting for detecting the kidney (location of the kidney) and calculation of the feature point statistical data may be performed using feature points pertaining to the kidney cortex excluding renal pelvis and renal sinus regions pertaining to the central region of the ultrasound kidney image.

The orientation data of the template kidney feature points, the template kidney periphery feature points, feature points of regions of interest of a patient having a normal fatty liver grade, and the template diaphragm feature points may be used after correction of the major rotational orientation to 0 degrees (0°).

It should be understood that the aforementioned solutions are provided for illustration only and are not to be construed in any way as limiting the present invention. In addition to the exemplary embodiments described above, other embodiments may exist in the drawings and detailed description of the invention.

As described above, the present invention provides an apparatus for automatic ultrasound diagnosis of liver steatosis using feature points in an ultrasound image, which can automatically determine a grade of liver steatosis, which is difficult to determine visually, through extraction from an image acquired by medical imaging, and a remote medical diagnosis method using the same.

However, it should be understood that the effects obtainable by the present invention are not limited to the aforementioned effects and other effects may exist.

BRIEF DESCRIPTION OF THE DRAWINGS

FIG. 3A and FIG. 3B are diagrams illustrating examples of calculation of a Euclidean distance between a first fitting curve and a second fitting curve obtained by curve fitting with respect to an imaginary closed loop obtained by connecting template kidney periphery feature points.

FIG. 4A is a diagram of a feature point detection unit of the automatic ultrasound diagnosis apparatus shown in FIG. 1 and FIG. 2.

FIG. 7 is a block diagram of an apparatus for automatic ultrasound diagnosis of liver steatosis using feature points in an ultrasound image according to another embodiment of the present invention.

FIG. 8A shows a process of obtaining an ultrasound image through semantic segmentation by the bad feature point removal unit according to one embodiment of the present invention.

FIG. 8B shows a process of obtaining an ultrasound image based on edge components by the bad feature point removal unit according to one embodiment of the present invention.

DETAILED DESCRIPTION

Figure 1:
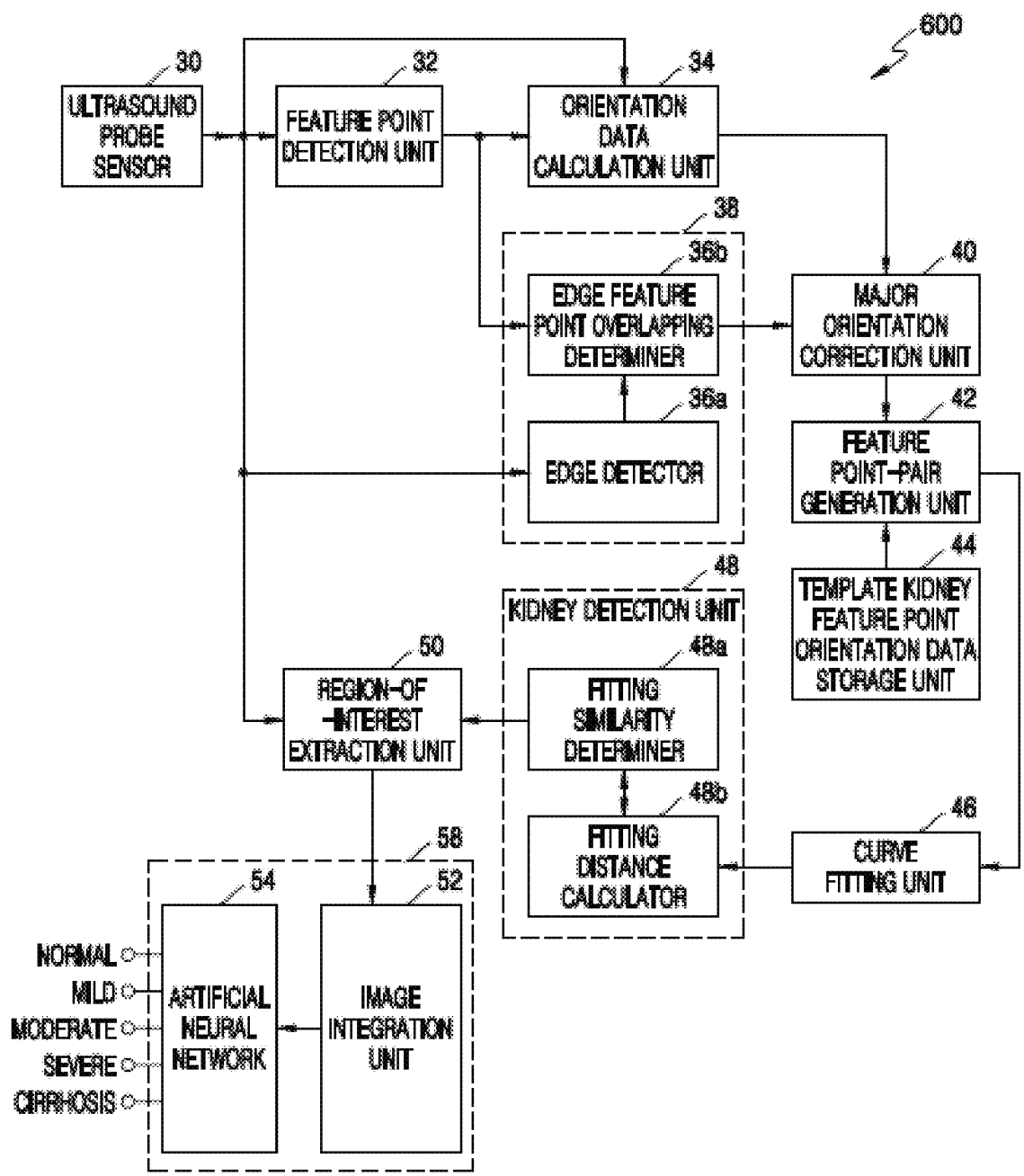
FIG. 1 and FIG. 2 are block diagrams of an apparatus for automatic ultrasound diagnosis of liver steatosis using feature points in an ultrasound image according to one embodiment of the present invention.

Now, exemplary embodiments of the present invention will be described in detail with reference to the accompanying drawings so that those skilled in the art can easily implement the present invention. It should be understood that the present invention is not limited to the following embodiments and may be embodied in different ways. In the drawings, portions irrelevant to the description will be omitted for clarity. Like components will be denoted by like reference numerals throughout the specification.

It will be understood that, when an element is referred to as being "connected to" another element, it can be directly connected to other element, or can be electrically or indirectly connected to the other element with a different element interposed therebetween.

It will be understood that when an element is referred to as being "on," "above," "at an upper end of," "under," "below," or "at a lower end of" another element, it may directly adjoin the other element or layer, or intervening elements may be present.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups.

Hereinafter, exemplary embodiments of the present invention will be described in detail with reference to the accompanying drawings.

Figure 2:
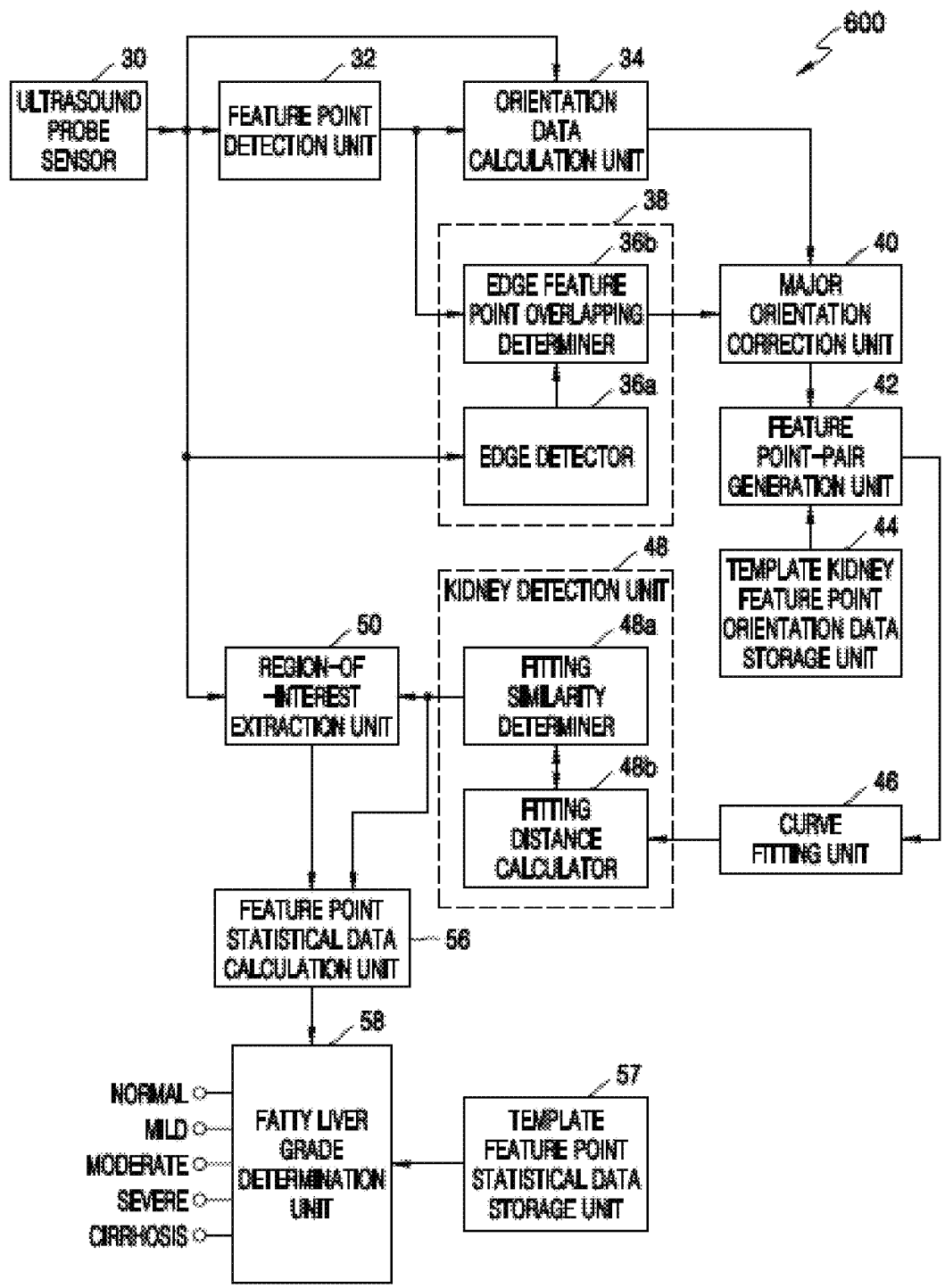

FIG. 1 and FIG. 2 are block diagrams of an apparatus 600 for automatic ultrasound diagnosis of liver steatosis using feature points in an ultrasound image according to one embodiment of the present invention. The automatic ultrasound diagnosis apparatus 600 according to this embodiment includes: an ultrasound probe sensor 30 acquiring an ultrasound image from a patient; a template kidney feature point orientation data storage unit 44 storing orientation data with respect to template kidney periphery feature points corresponding to feature points of a kidney periphery in template ultrasound pictures and pixels in a patch image of each of the feature points; a feature point detection unit 32 detecting feature points in the ultrasound image; an orientation data calculation unit 34 calculating orientation data with respect to pixels in a patch image of each of the feature points of the ultrasound image; a bad feature point removal unit 38 including an edge detector 36a adapted to detect edge components of the ultrasound image and an edge feature point overlapping determiner 36b adapted to determine whether the edge components overlap the feature points of the ultrasound image on two-dimensional ultrasound image space coordinates to locate feature points for comparison through removal of bad feature points from the feature points of the ultrasound image, the bad feature points being determined by considering feature points of the ultrasound image not overlapping the edge components to be the bad feature points; a major orientation correction unit 40 correcting orientations of pixels in a patch image of each of the feature points for comparison using a major rotational orientation corresponding to the most frequent orientation in a histogram indicating the frequency of pixels with respect to an orientation, based on orientation data with respect to the pixels in the patch image of each of the feature points for comparison; a feature point-pair generation unit 42 generating a pair of feature points between the template kidney periphery feature points and the feature points for comparison pertaining to patch images having high similarity through comparison between the orientation data with respect to the pixels in the patch images of the template kidney periphery feature points and in the patch images of the feature points for comparison; a curve fitting unit 46 generating a first fitting curve through ellipse fitting or curve fitting with respect to the feature points for comparison paired with the template kidney periphery feature points, or calculating the number of fitting feature points corresponding to the number of feature points overlapping each other on two-dimensional space coordinates through scanning comparison between a template edge component and the feature points for comparison paired with the template kidney periphery feature points by the feature point-pair generation unit; a kidney detection unit 48 detecting a location of the kidney from the ultrasound image based on the first fitting curve or the number of fitting feature points; and a region-of-interest extraction unit 50 extracting images of one or more regions of interest through space addressing on the ultrasound image with reference to the detected kidney (location of the kidney).

Referring to FIG. 1, the automatic ultrasound diagnosis apparatus 600 according to this embodiment includes an image integration unit 52 concatenating images of the regions of interest in the template ultrasound pictures or in the ultrasound image into one integrated image; and a fatty liver grade determination unit 58 constituted by an artificial neural network 54 trained on the integrated image by deep learning, whereby the deep learning-trained artificial neural network 54 can automatically determine a grade of liver steatosis of the patient based on the ultrasound image of the patient input from the ultrasound probe sensor 30.

Referring to FIG. 2, the automatic ultrasound diagnosis apparatus 600 according to another embodiment includes: a template feature point statistical data storage unit 57 storing template feature point statistical data comprising statistical data with respect to feature points of a kidney region in the template ultrasound pictures and feature points of regions of interest excluding the kidney region; a feature point statistical data calculation unit 56 calculating feature point statistical data from the feature points of the kidney region detected by the kidney detection unit 48 or from the feature points of the regions of interest extracted by the region-of-interest extraction unit 50; and a fatty liver grade determination unit 58 determining a grade of liver steatosis classified into a mild grade, a moderate grade, a severe grade, and a cirrhosis grade, based on the template feature point statistical data and the feature point statistical data calculated by the feature point statistical data calculation unit 56, thereby achieving automatic determination of the grade of liver steatosis of the patient based on the ultrasound images of the patient input from the ultrasound image sensor.

The automatic ultrasound diagnosis apparatus 600 according to the embodiment shown in FIG. 1 may further include a template region-of-interest orientation displacement storage unit (not shown) obtaining candidate orientations having the maximum magnitudes from each of patch images of the feature points of the regions of interest in the template ultrasound pictures having a normal grade of liver steatosis and storing orientation displacement data corresponding to an orientation difference between the maximum orientation and the minimum orientation among the candidate orientations, and the fatty liver grade determination unit 58 may detect the feature points of the regions of interest from the ultrasound image of the patient to determine the grade of liver steatosis based on the number of fatty liver feature points corresponding to feature points, which are included in the regions of interest of the ultrasound image of the patient and deviate from the range of the orientation displacement data stored in the template region-of-interest orientation displacement storage unit.

The curve fitting unit 46 adapted to calculate the number of fitting feature points may calculate the number of fitting feature points corresponding to the number of feature points overlapping each other on the two-dimensional space coordinates through scanning comparison between a template edge component comprising the template kidney periphery feature points and the feature points for comparison paired with the template kidney periphery feature points by the feature point-pair generation unit 42, and the kidney detection unit 48 detects a location of the kidney from the ultrasound image based on the number of fitting feature points. The kidney detection unit 48 may determine that a kidney is present at a coordinate location at which the number of fitting feature points is a predetermined number or more and reaches the maximum value.

FIG. 3A and FIG. 3B are diagrams illustrating examples of calculation of a Euclidean distance between a first fitting curve 231 and a second fitting curve 232 obtained by curve fitting with respect to an imaginary closed loop obtained by connecting the template kidney periphery feature points. More specifically, FIG. 3A and FIG. 3B illustrate two examples of a method of calculating the distance between the first fitting curve 231 and the second fitting curve 232 using a fitting distance calculator 46b shown in FIG. 2.

Here, a closed loop shape formed by the second fitting curve 232 will be referred to as Object A2 (302) and a closed loop shape formed by the first fitting curve 231 will be referred to as Object A1 (301).

FIG. 3A illustrates an example of calculation of the Euclidean distance between the first fitting curve 231 and the second fitting curve 232 after alignment of these fitting curves using a correlation coefficient between the first fitting curve 231 and the second fitting curve 232. Referring to FIG. 3A, calculation of the Euclidean distance between the first fitting curve 231 and the second fitting curve 232 may be performed by aligning the first fitting curve 231 with the second fitting curve 232 at a location where the correlation coefficient between Object A1 (301) and Object A2 (302) reaches the maximum value, followed by obtaining the sum of absolute values of distance differences between the first fitting curve 231 and the second fitting curve 232 while rotating the fitting curves about the center of gravity of the second fitting curve 232 by 360 degrees.

FIG. 3B illustrates an example of calculation of the Euclidean distance between the first fitting curve 231 and the second fitting curve 232 after alignment of these fitting curves using the center of gravity of the first fitting curve 231 and the second fitting curve 232. Referring to FIG. 3B, calculation of the Euclidean distance between the first fitting curve 231 and the second fitting curve 232 may be performed by aligning the first fitting curve 231 with the second fitting curve 232 such that the center 240b of gravity of Object A1 is coincident with the center 250a of gravity of Object A2, followed by obtaining the sum of absolute values of distance differences between the first fitting curve 231 and the second fitting curve 232 while rotating the fitting curves about the center of gravity of the second fitting curve 232 by 360 degrees.

FIG. 4A is a diagram of one embodiment of the feature point detection unit 32 of the automatic ultrasound diagnosis apparatus 600 shown in FIG. 1 and FIG. 2. Referring to FIG. 4A, the feature point detection unit 32 may include: a Gaussian filter unit 80 including a first Gaussian filter 81 composed of Standard deviation 1 generating a first Gaussian image 91 from the ultrasound image, a second Gaussian filter 82 composed of Standard deviation 2 generating a second Gaussian image 92 and having a greater value than Standard deviation 1, a third Gaussian filter 83 composed of Standard deviation 3 generating a third Gaussian image 93 and having a greater value than Standard deviation 2, a fourth Gaussian filter 84 composed of Standard deviation 4 generating a fourth Gaussian image 94 and having a greater value than Standard deviation 3, a fifth Gaussian filter 85 composed of Standard deviation 5 generating a fifth Gaussian image 95 and having a greater value than Standard deviation 4, and a sixth Gaussian filter 86 composed of Standard deviation 6 generating a sixth Gaussian image 96 and having a greater value than Standard deviation 5; a pixel subtractor 99 performing subtraction for each pixel between the first Gaussian image 91 and the second Gaussian image 92 to obtain a first differential image 101, performing subtraction for each pixel between the second Gaussian image 92 and the third Gaussian image 93 to obtain a second differential image 102, performing subtraction for each pixel between the third Gaussian image 93 and the fourth Gaussian image 94 to obtain a third differential image 103, performing subtraction for each pixel between the fourth Gaussian image 94 and the fifth Gaussian image 95 to obtain a fourth differential image 105, and performing subtraction for each pixel between the fifth Gaussian image 95 and the sixth Gaussian image 95 to obtain a fifth differential image 106; and a maximum-minimum pixel detector 108 generating a first scan window, a second scan window, and a third scan window each having a size of 3×3 for scanning through parallel synchronization of the second differential image 102 together with the differential images (first differential image 101 and third differential image 103) adjacent thereto, and determining the maximum or minimum pixel based on the feature points during parallel scanning of adjacent differential images using the scan windows, thereby generating (detecting) the locations of the feature points.

Figure 4B:
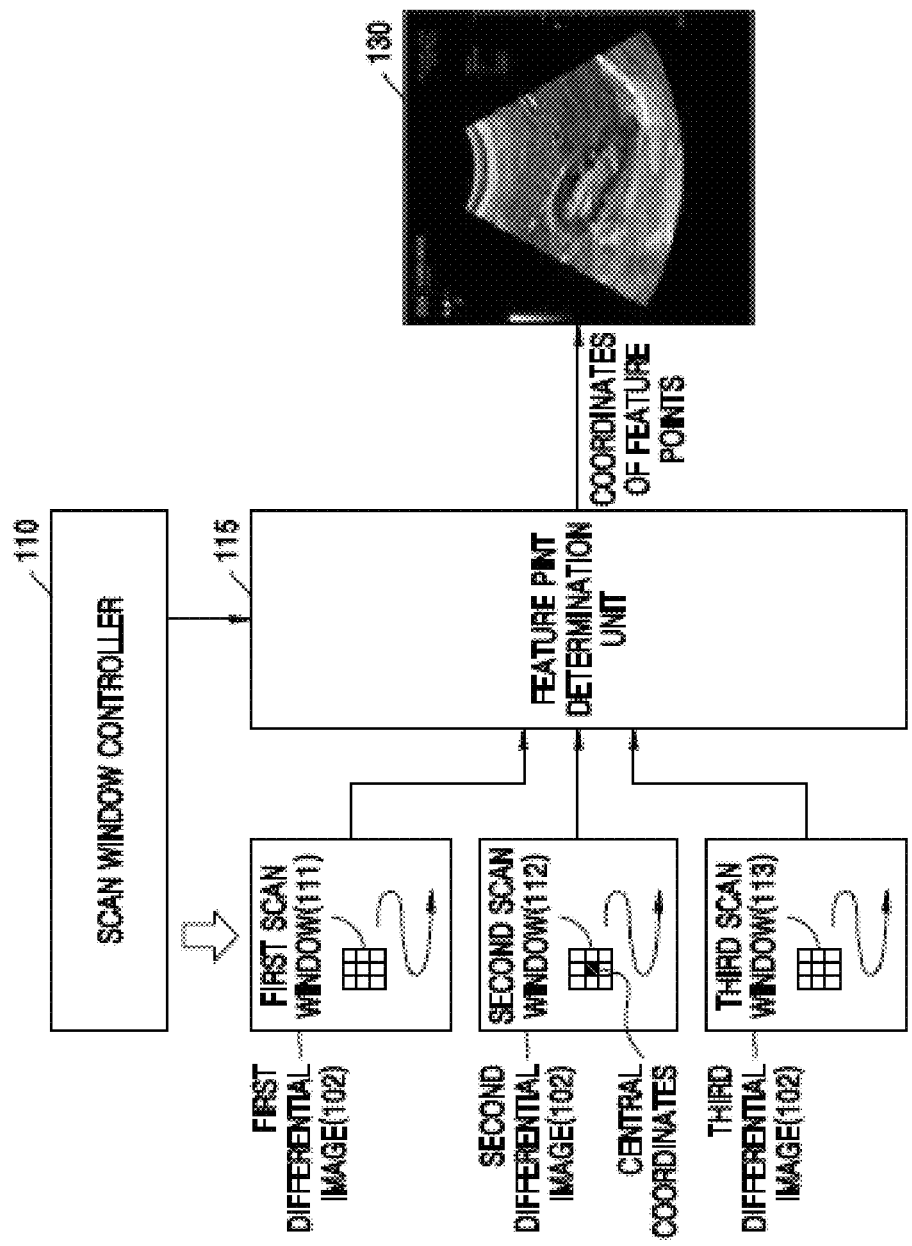
FIG. 4B is a diagram of a maximum-minimum pixel detector of the feature point detection unit shown in FIG. 4A.

FIG. 4B is a diagram of one embodiment of the maximum-minimum pixel detector 108. Referring to FIG. 4B, the maximum-minimum pixel detector 108 may include: a scan window controller 110 generating and controlling a first scan window 111, a second scan window 112, and a third scan window 113 each having a size of 3×3 for scanning through parallel synchronization of the second differential image 102 with the differential images (first differential image 101 and third differential image 103) directly adjacent thereto in the horizontal or vertical direction; and a feature point determiner 115 determining whether a pixel value of the central coordinates of the second scan window 112 is the maximum value or the minimum value among all pixel values (26 pixels) in the first to third scan windows, and determining that a feature point of the pixel value is an effective feature point if the pixel value is greater than or equal to a feature point determination reference value, thereby providing coordinate location data of the feature points in the ultrasound image. In addition, FIG. 4B shows one example of an ultrasound image 130 in which "+" marks overlap at a location of a feature point according to the coordinate location data of the obtained feature point.

Figure 5:
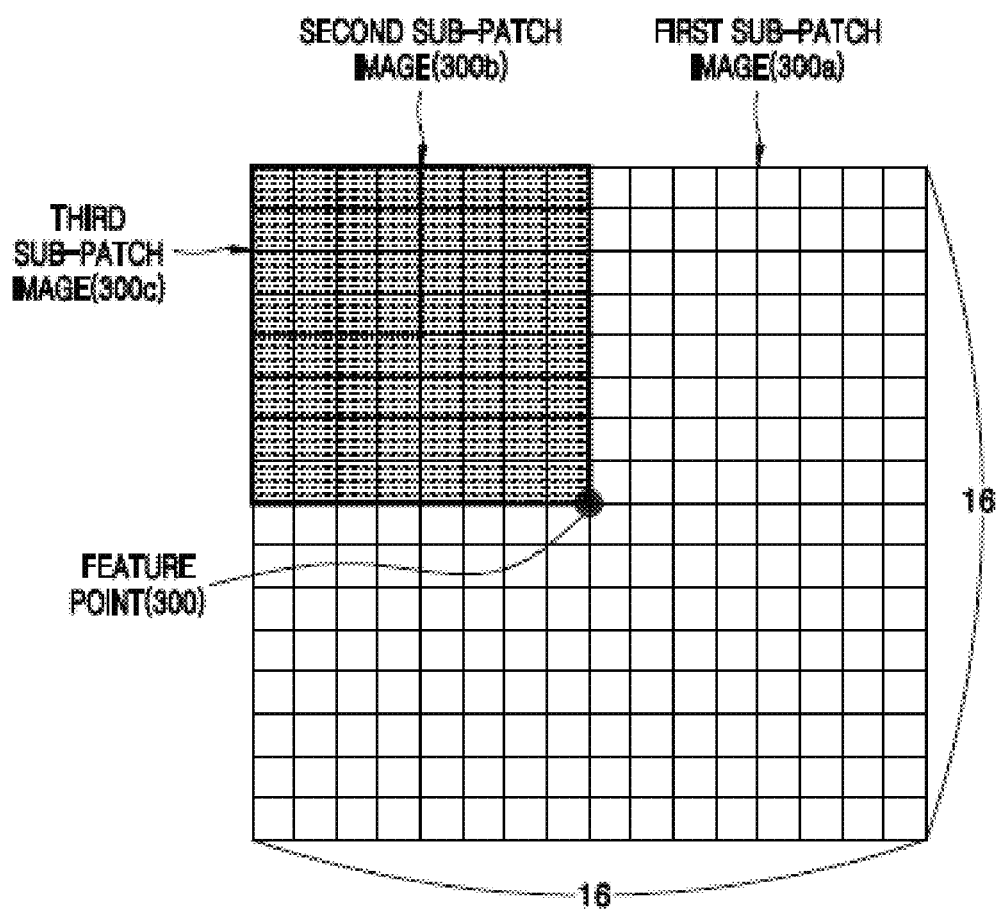
FIG. 5 shows one example of patch images constituted by 16×16 pixels around a feature point.

FIG. 5 shows one example of patch images constituted by 16×16 pixels around a feature point 300. The patch images may be composed of at least one image selected from the group of a first sub-patch image 300a, a second sub-patch image 300b and a third sub-patch image 300c.

In this example, the first sub-patch image 300a is composed of 16×16 pixels around the feature point 300, the second sub-patch image 300b comprises 4 sub-images each composed of 8×8 pixels and obtained by quartering the first sub-patch image composed of 16×16 pixels around the feature point 300, and the third sub-patch image 300c comprises 16 sub-images each composed of 4×4 pixels and obtained by dividing the first sub-patch image composed of 16×16 pixels around the feature point 300 into 16 equal parts.

Figure 6:
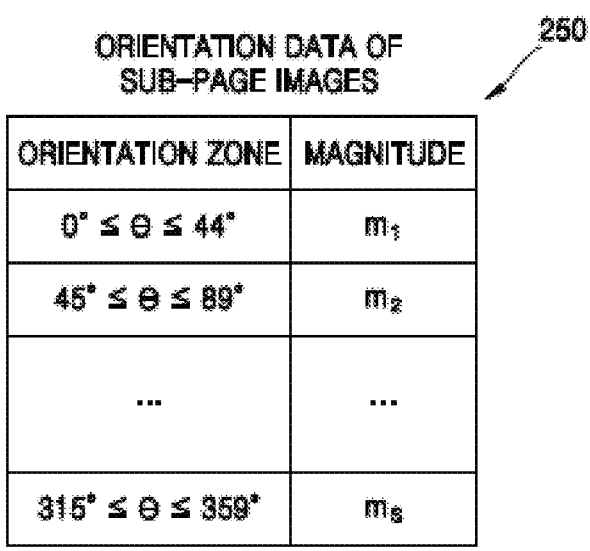
FIG. 6 shows a table of orientation data {θ(x, y), m(x, y)} obtained by calculating a Gradient direction θ(x, y) and a magnitude m(x, y) for each pixel on a sub-patch image, and adding up the magnitudes m(x, y) of pixels having similar Gradient directions θ(x, y).

FIG. 6 shows a table 250 of orientation data {θ(x, y), m(x, y)} obtained by calculating a Gradient direction θ(x, y) and a magnitude m(x, y) for each pixel on a sub-patch image, and adding up the magnitudes m(x, y) of pixels having similar Gradient directions θ(x, y).

According to this embodiment, the similar Gradient directions θ(x, y) may be assigned at intervals of 45 degrees. In this case, eight orientation zones, such as 0°≤θ≤44°, 45°≤θ≤89°, . . . , and 315°≤θ≤359°, are generated. Referring to FIG. 6, the sum of the magnitudes m(x, y) having the Gradient directions θ(x, y) pertaining to the zone of 0°≤θ≤44° is m1 and the sum of the magnitudes m(x, y) having the Gradient directions θ(x, y) pertaining to the zone of 45°≤θ≤89° is m2.

Accordingly, a single sub-patch image has 8 orientation data.

If the second sub-patch image is used for calculation of the orientation data, each feature point includes a total of 32 orientation data since each feature point includes 4 second sub-patch images.

FIG. 7 is a block diagram of an apparatus 600 for automatic ultrasound diagnosis of liver steatosis using feature points in an ultrasound image according to another embodiment of the present invention. The automatic ultrasound diagnosis apparatus 600 according to this embodiment includes: an ultrasound probe sensor 30 acquiring an ultrasound image from a patient; a template diaphragm feature point orientation data storage unit 44a storing orientation data with respect to template diaphragm feature points corresponding to feature points of the diaphragm included in template ultrasound pictures and pixels in a patch image of each of the feature points; a template diaphragm orientation displacement storage unit 38a obtaining candidate orientations having the maximum magnitudes from each of the patch images corresponding to the template diaphragm feature points and storing orientation displacement data corresponding to a difference between the maximum orientation and the minimum orientation among the candidate orientations as the range of template diaphragm orientation displacement; a feature point detection unit 32 detecting feature points in the ultrasound image; an orientation data calculation unit 34 calculating orientation data with respect to pixels in a patch image of each of the feature points of the ultrasound image; a bad feature point removal unit 38 removing bad feature points from the feature points obtained from the ultrasound image to locate feature points for comparison, the bad feature points being determined by considering feature points of the ultrasound image deviating from a template diaphragm orientation displacement range to be the bad feature points; a major orientation correction unit 40 obtaining the most frequent orientation as a major rotational orientation in a histogram indicating the frequency of pixels with respect to an orientation, based on orientation data with respect to pixels in a patch image of each of the feature points for comparison, and correcting orientations of the pixels in the patch image of each of the feature points for comparison based on the major rotational orientation; a feature point-pair generation unit 42a generating a pair of feature points between the feature points using patch images having high similarity through comparison between the orientation data with respect to the pixels in the patch images of the template diaphragm feature points and in the patch images of the feature points for comparison; a curve fitting unit 46a obtaining a curve fitting curve through curve fitting with respect to the feature points for comparison paired with the template diaphragm feature points; a diaphragm image extraction unit 62 extracting an image of a diaphragm region from the curve fitting curve; a fitting distance calculator 48c calculating a Euclidean distance between the curve fitting curve and the feature points for comparison applied to curve fitting; a liver region image extraction unit 60 extracting an image of a liver region from the ultrasound image through detection of a location of the liver region based on a location of the extracted image of the diaphragm region; and a fatty liver grade determination unit 58a determining a grade of liver steatosis classified into a mild grade, a moderate grade, a severe grade, and a cirrhosis grade, based on a "brightness ratio of the liver region to the diaphragm region" obtained by calculating an average brightness of pixels in the extracted image of the liver region and an average brightness of pixels in the extracted image of the diaphragm region, whereby the grade of liver steatosis of the patient can be automatically determined based on the "brightness ratio of the liver region to the diaphragm region" obtained from the ultrasound image of the patient input from the ultrasound probe sensor 30.

FIG. 8A shows one embodiment of a process of obtaining an ultrasound image through semantic segmentation using the bad feature point removal unit 38 according to the present invention, in which an ultrasound image 120a labeled with different colors for organs is obtained through semantic segmentation with respect to an ultrasound image 22 of a parasagittal scan plane by the bad feature point removal unit 38.

Reference numeral 26 indicates the liver, Reference numeral 25 indicates the spleen, Reference numeral 24 indicates the kidney, and Reference numeral 23 indicates the diaphragm.

Referring to FIG. 8A, for example, the bad feature point removal unit 38 may detect the kidney region 24 through semantic segmentation of the ultrasound image 22 of the patient sent from the ultrasound probe sensor 30 and remove the bad feature points from an ultrasound image 130 in which feature points overlapping each other in the ultrasound image of the patient are detected by the feature point detection unit 32. Here, the bad feature point removal unit 38 may locate the feature points for comparison through removal of the bad feature points from the feature points of the ultrasound image by considering the feature points of the ultrasound image excluding the feature points of the kidney region 24 subjected to semantic segmentation to be the bad feature point (indicated by "Δ"). Reference numeral 132a indicates one example in which the feature points for comparison (indicated by "x") obtained by removing the bad feature points overlap each other in the ultrasound image.

FIG. 8B shows a process of obtaining an ultrasound image based on edge components by the bad feature point removal unit according to one embodiment of the present invention, in which an ultrasound image 120b is obtained through extraction of the edge components from an ultrasound image 22 of a parasagittal scan plane by the bad feature point removal unit 38.

Referring to FIG. 8B, for example, the bad feature point removal unit 38 may detect the edge components of the ultrasound image 22 of the patient sent from the ultrasound probe sensor 30 and remove the bad feature points in the ultrasound image 130 in which feature points overlapping each other in the ultrasound image of the patient are detected by the feature point detection unit 32. Here, the bad feature point removal unit 38 may locate the feature points for comparison through removal of the bad feature points from the feature points of the ultrasound image 130 by considering the feature points marked in the ultrasound image 130 excluding the edge components to be the bad feature point (indicated by "Δ"). Reference numeral 132b indicates one example in which the feature points for comparison (indicated by "x") obtained by removing the bad feature points overlap each other in the ultrasound image.

Figure 8C:
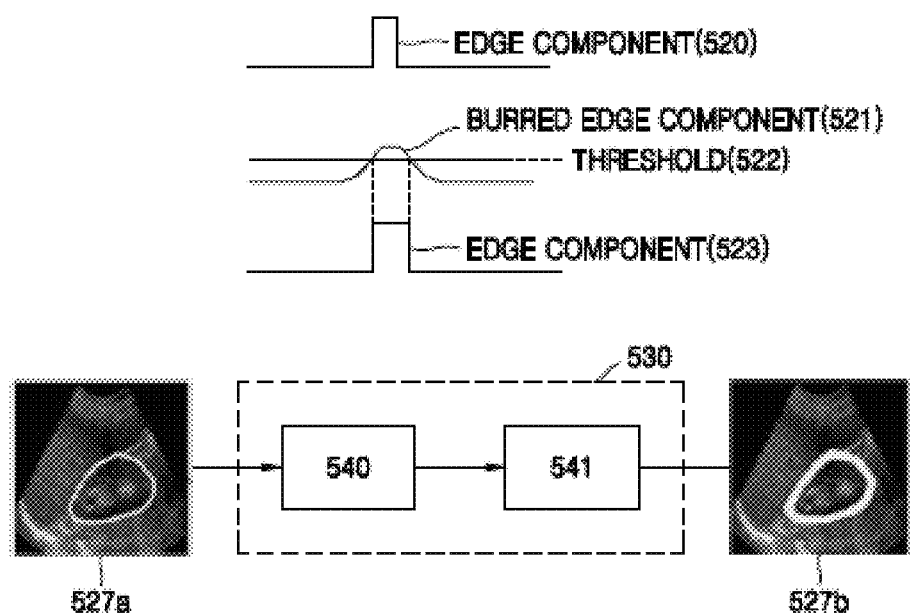
FIG. 8C is a diagram illustrating one embodiment of an edge width expander according to the present invention, which generates a width-expanded edge component through expansion of a width of an edge component detected by an edge detector in a two-dimensional space.

FIG. 8C is a diagram illustrating one embodiment of an edge width expander 530 according to the present invention, which generates a width-expanded edge component 523 through expansion of a width of an edge component 520 detected by an edge detector in a two-dimensional space. Referring to FIG. 8C, the edge width expander 530 may include a low pass filter 540 adapted to obtain a blurred edge component 521 from the detected edge component 520 and an edge determiner 541 adapted to set a threshold value for regulation of an expanded width with respect to the blurred edge component 521 and to obtain the width-expanded edge component 523 by determining only the edge component having a value greater than or equal to the threshold value as the edge component.

Reference numeral 527a indicates an ultrasound image comprising an actual edge component 520 detected by the edge detector and Reference numeral 537b indicates an ultrasound image comprising an edge component 523 having an expanded width through expansion of the width of the edge component 520 detected by the edge detector 530.

When the expanded edge component 523 is used instead of the actual edge component 520, it is possible to prevent feature points immediately adjacent to the actual edge component 520 from being removed unfortunately (even though it is desirable that the feature points immediately adjacent to the actual edge component be not be removed), thereby providing an advantage in curve fitting and detection of the kidney.

Figure 8D:
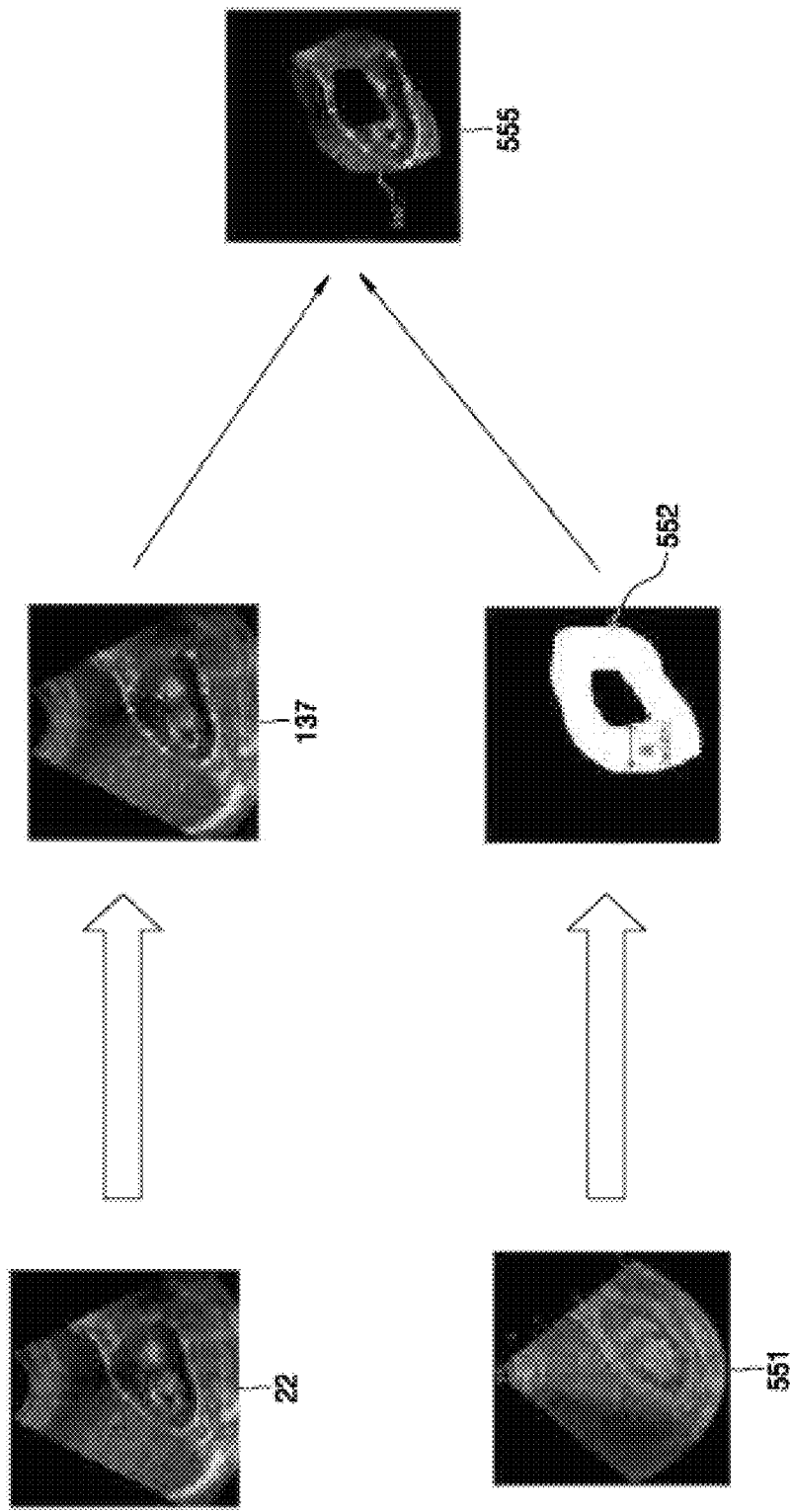
FIG. 8D is a diagram illustrating one embodiment of a process of calculating the number of fitting feature points overlapping each other on a two-dimensional space coordinates through scanning comparison between final feature points and a template edge component.

FIG. 8D is a diagram illustrating one embodiment of a process of calculating the number of fitting feature points overlapping each other on a two-dimensional space coordinates through scanning comparison between a template edge component 552 and final feature points (that is, final feature point, indicated by "x") paired with the template kidney periphery feature points by the feature point-pair generation unit 42.

The template edge 552 refers to an edge component comprising all feature points of the kidney periphery in a template ultrasound picture 551.

The width of the template edge may be set to be greater than an actual edge width in consideration of various changes of the ultrasound image (variation possibility), that is, diversity thereof, to be advantageous in detection of the kidney upon scanning. In other words, expansion of the width of the template edge can prevent removal of feature points which will be used for detection of the kidney, thereby allowing easier detection of the kidney.

Reference 555 indicates an ultrasound image in which the number of fitting feature points overlapping each other reaches the maximum number upon scanning comparison between an image 137 having final feature points (indicated by "x") marked thereon and the template edge 552. It can be confirmed that a number of final feature points overlap with each other on the template edge 552.

Figure 8E:
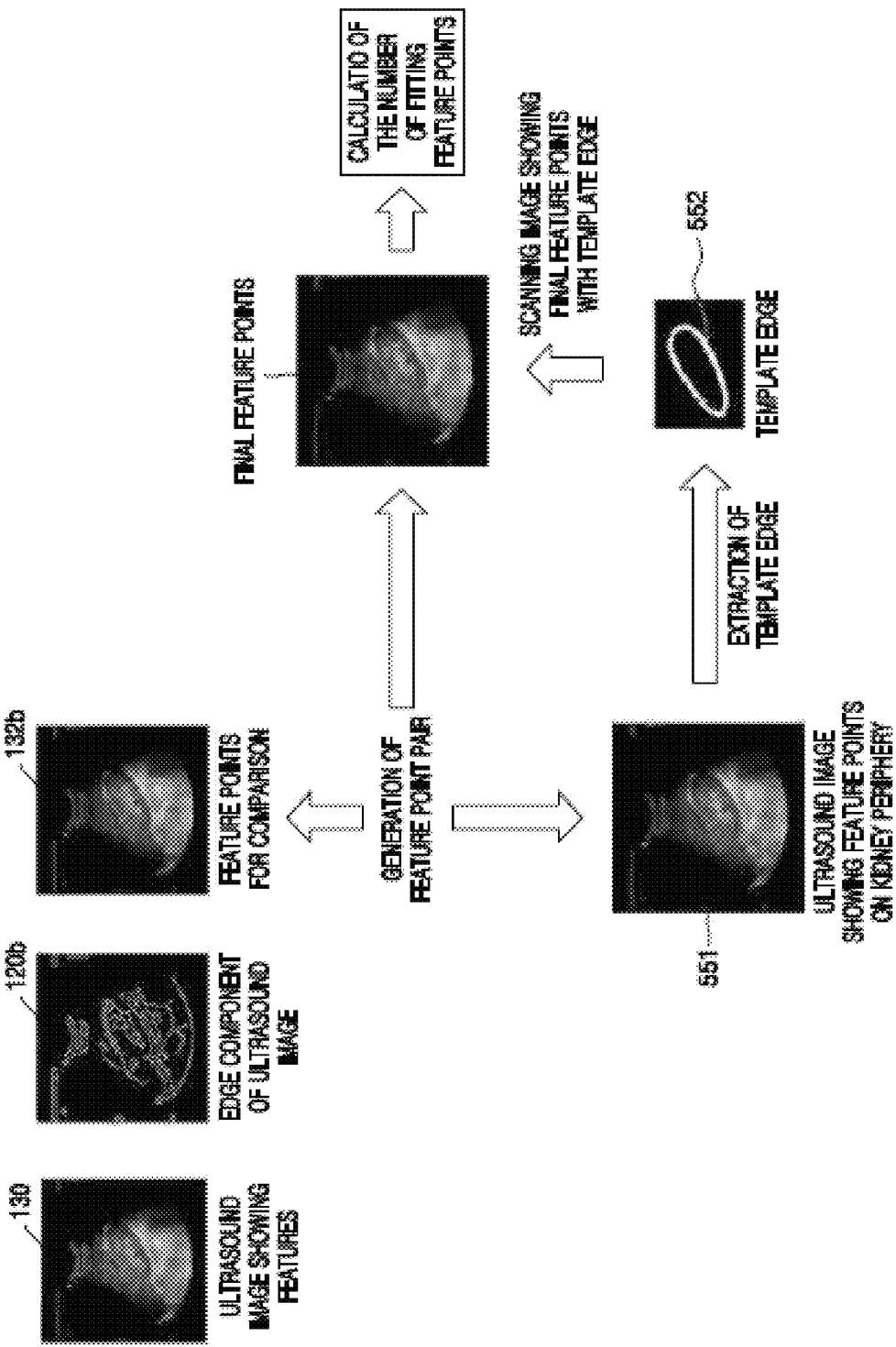
FIG. 8E is a diagram illustrating one embodiment of a process of detecting a location of the kidney in an ultrasound image through calculation of the number of fitting feature points from final feature points using a template edge 522.

FIG. 8E is a diagram illustrating one embodiment of a process of detecting a location of a kidney in the ultrasound image through calculation of the number of fitting feature points from final feature points 137 using the template edge 552.

Reference 130 indicates an ultrasound image on which feature points detected in the ultrasound image by the feature point detection unit 32 overlap.

Reference numeral 120b indicates an edge component of the ultrasound image.

Reference numeral 132b shows one example of a process of locating the feature points for comparison by removing the bad feature points from the feature points of the ultrasound image 130 by considering the feature points of the ultrasound image 130 excluding the feature points in the region of the edge component 120b to be the bad feature point. It can be confirmed that many bad feature points are removed from the feature points 130 of the ultrasound image 130.

Then, the feature points for comparison paired with the template kidney periphery feature points by the feature point-pair generation unit 42 may be located. The feature points for comparison paired with the template kidney periphery feature points become final feature points 137.

Since the final feature points 137 are paired with the template kidney periphery feature points, the possibility of the presence of the final feature points on the kidney periphery of the ultrasound image is further increased.

Then, the template edge 552 including all of the feature points of the kidney periphery in the template ultrasound picture 551 may be extracted.

Then, the curve fitting unit 46 may calculating the number of fitting feature points overlapping on the two-dimensional space coordinates through scanning comparison between the final feature points 137 and the template edge component 552.

Upon scanning comparison between the final feature points 137 and the template edge component 552, the location of the coordinates at which the number of fitting feature point overlapping each other becomes the location of the kidney.

Figure 9:
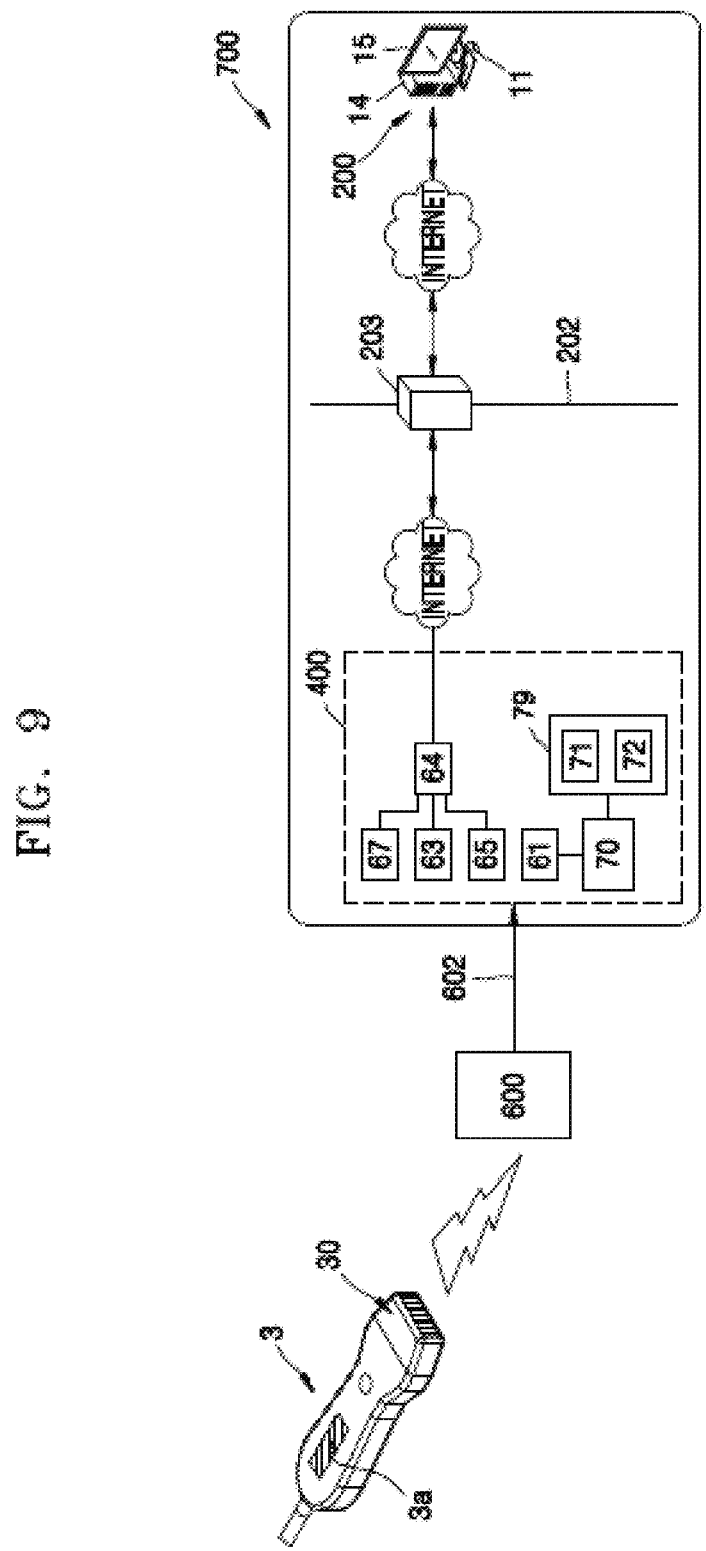
FIG. 9 is a diagram of an apparatus for automatic ultrasound diagnosis of liver steatosis using feature points in an ultrasound image according to a further embodiment of the present invention, which is connected to a remote medical diagnosis system to perform automatic diagnosis of medical imaging data of a patient through an AI-based virtual doctor residing in the remote medical diagnosis system.

FIG. 9 is a diagram of an apparatus 600 for automatic ultrasound diagnosis of liver steatosis using feature points in an ultrasound image according to a further embodiment of the present invention, which is connected to a remote medical diagnosis system 700 to perform automatic diagnosis of medical imaging data of a patient through an AI-based virtual doctor 79 residing in the remote medical diagnosis system 700. Referring to 9, the remote medical diagnosis system 700 according to this embodiment may include: an ultrasound medical device 3 provided with an ultrasound probe sensor 30; a wireless transmitter 3a integrated into the ultrasound medical device 3 to wirelessly transmit medical image data of a patient measured by the ultrasound medical device 3; the automatic ultrasound diagnosis apparatus 600 according to the present invention, the automatic ultrasound diagnosis apparatus receiving an ultrasound image of the patient from the wireless transmitter 3a and automatically determining a grade of liver steatosis; a user terminal 400 including a camera 61 monitoring use of the ultrasound medical device 3, a first authentication unit 67 wirelessly authenticating a product ID of the ultrasound medical device 3, a recording unit 63 storing the ultrasound image of the patient obtained by the ultrasound medical device 3, an Internet connector 64 transmitting the ultrasound image and the product ID of the ultrasound medical device 3 to a remote diagnosis server 203 via a communication network 202 and providing a communication channel for a remote consultation service, and a first consultation service unit providing a consultation service with a medical expert; a communication interface 602 providing a connection to the automatic ultrasound diagnosis apparatus 600 and the user terminal 400; an artificial neural network 70 residing as software in the user terminal 400 and trained on a medical image database accumulated by the ultrasound medical device 3 by deep learning; a virtual doctor 79 residing as software in the user terminal 400 and including a guide unit 71 guiding or instructing how to use the ultrasound medical device 3 and a diagnosis unit 72 outputting a diagnostic result obtained through automatic analysis of the medical image data of the patient obtained by the ultrasound medical device 3 using the deep learning-trained artificial neural network 70; and a medical expert terminal 200 including a receiver (not shown) receiving the medical image data and the ultrasound image via the communication network 202 and a second consultation service unit providing a consultation service between a user and a medical expert.

The guide unit 71 serves to guide or instruct a user on how to use the ultrasound medical device 3 based on results of monitoring use of the ultrasound medical device 3 in real time using the camera 61.

The medical expert terminal 200 may further include a camera 14, a microphone 15, and a mouse 11.

Next, based on the details described above, an apparatus 600 for automatic ultrasound diagnosis of liver steatosis using feature points in an ultrasound image (hereinafter referred to as the automatic ultrasound diagnosis apparatus) according to various embodiments of the present invention will be briefly discussed.

An apparatus 600 for automatic ultrasound diagnosis of liver steatosis using feature points in an ultrasound image (hereinafter referred to as the automatic ultrasound diagnosis apparatus) according to one embodiment of the present invention may include an ultrasound probe sensor 30, a template kidney feature point orientation data storage unit 44, a feature point detection unit 32, an orientation data calculation unit 34, a bad feature point removal unit 38, a major orientation correction unit 40, a feature point-pair generation unit 42, a curve fitting unit 46, a kidney detection unit 48, a region-of-interest extraction unit 50, and a fatty liver grade determination unit 58.

The ultrasound probe sensor 30 may obtain an ultrasound image from a patient. In other words, the ultrasound probe sensor 30 may acquire the ultrasound image of the patient.

The template kidney feature point orientation data storage unit 44 may store orientation data with respect to template kidney periphery feature points corresponding to feature points of the kidney periphery in template ultrasound pictures and pixels in a patch image of each of the feature points.

Herein, a small image obtained by collecting pixels around a feature point of an ultrasound image will be referred to as a patch image.

Herein, the template ultrasound picture means an ultrasound picture of a normal fatty liver grade.

The orientation data may be defined as the same orientation data as or similar orientation data to the orientations calculated with respect to the feature points by the orientation data calculation unit 34.

The feature point detection unit 32 may detect the feature point from the ultrasound image or from an edge component of the ultrasound image. In other words, the feature point detection unit 32 may detect (extract) the feature points in the ultrasound image or from the edge component of the ultrasound image.

Referring to FIG. 4A, the feature point detection unit 32 may include a Gaussian filter unit 80, a pixel subtractor 99, and a maximum-minimum pixel detector 108.

The Gaussian filter unit 80 may generate a Gaussian image. Referring to FIG. 4A, for example, the Gaussian filter unit 80 may include a first Gaussian filter 81 generating a first Gaussian image 91, a second Gaussian filter 82 generating a second Gaussian image 92, a third Gaussian filter 83 generating a third Gaussian image 93, a fourth Gaussian filter 84 generating a fourth Gaussian image 94, a fifth Gaussian filter 85 generating a fifth Gaussian image 95, and a sixth Gaussian filter 96 generating a sixth Gaussian image 96.

The pixel subtractor 99 may perform subtraction for each pixel between the Gaussian images to acquire differential images. Referring to FIG. 4A, for example, the pixel subtractor 99 may perform subtraction for each pixel between the first Gaussian image 91 and the second Gaussian image 92 to obtain a first differential image 101. In addition, the pixel subtractor 99 may perform subtraction for each pixel between the first Gaussian image 91 and the second Gaussian image 92 to acquire a first differential image 101. In addition, the pixel subtractor 99 may perform subtraction for each pixel between the second Gaussian image 92 and the third Gaussian image 93 to acquire a second differential image 102. In addition, the pixel subtractor 99 may perform subtraction for each pixel between the third Gaussian image 93 and the fourth Gaussian image 94 to acquire a third differential image 103. In addition, the pixel subtractor 99 may perform subtraction for each pixel between the fourth Gaussian image 94 and the fifth Gaussian image 95 to acquire a fourth differential image 105. In addition, the pixel subtractor 99 may perform subtraction for each pixel between the fifth Gaussian image 95 and the sixth Gaussian image 95 to acquire a fifth differential image 106.

Referring to FIG. 4A, the maximum-minimum pixel detector 108 may include a scan window controller 110 and a feature point determiner 115.

The scan window controller 110 may generate and control scan windows for scanning through parallel synchronization of a differential image together with other differential images directly adjacent thereto in the horizontal or vertical direction to detect the feature points in the ultrasound image. In other words, the scan window controller 110 may generate and control scan windows for scanning through parallel synchronization of a differential image together with other differential images directly adjacent thereto in the horizontal or vertical direction. Here, a plurality of scan windows may be generated. Referring to FIG. 4B, for example, the scan window controller 110 may generate and control a first scan window 111, a second scan window 112, and a third scan window 113 each having a size of 3×3 for scanning through parallel synchronization of the second differential image 102 and the differential images, that is, the first differential image 101 and the third differential image 103, directly adjacent thereto in the horizontal or vertical direction.

The feature point determiner 115 may determine whether a pixel value of the central coordinates of a certain scan window generated by the scan window controller 110 is the maximum value or the minimum value among all pixel values of the scan windows, and may determine that a feature point of the pixel value is an effective feature point if the pixel value is greater than or equal to a feature point determination reference value. Referring to FIG. 4B, for example, the feature point determiner 115 may determine whether a pixel value of the central coordinates of the second scan window 112 is the maximum value or the minimum value among all pixel values (26 pixels) in the first to third scan windows. Here, the pixel value corresponding to the central coordinates among all of the pixel values in the scan windows may be excluded. In addition, the feature point determiner 115 may determine that a feature point of the pixel value at the central coordinates is an effective feature point if an absolute value of the pixel value at central coordinates is greater than or equal to a feature point determination reference value. The feature point detection unit 32 may provide coordinate location data of the feature points in the ultrasound image, which are determined to be the effective feature points. FIG. 4B shows one example of an ultrasound image 130 in which "+" marks overlap at a location of a feature point according to the coordinate location data of the obtained feature point.

The orientation data calculation unit 34 may calculate orientation data with respect to pixels in each of patch images of feature points in an ultrasound image. Herein, the orientation data is defined as a set $\{m(x, y), \theta(x, y)\}$ of Gradient directions $\theta(x, y)$ and magnitudes $m(x, y)$ calculated from pixels in a patch image and is calculated by the following equation. <Equation>

$$m(x, y) = \sqrt{(L(x+1,y)-L(x-1,y))^2+(L(x,y+1)-L(x,y-1))^2}$$

$$\theta(x, y) = \tan^{-1}((L(x, y+1)-L(x, y-1))/(L(x+1, y)-L(x-1, y)))$$

In this equation, $L(x, y)$ may indicate the intensity of a pixel in a Gaussian image at the pixel coordinates $(x, y)$ in a patch image.

The magnitude component of the Gradient direction $\theta(x, y)$ is determined by the magnitude at the corresponding coordinates $(x, y)$.

Referring to FIG. 5, for example, for calculation of the orientation data $\{m(x, y), \theta(x, y)\}$ of the feature points, the orientation data calculation unit 34 may constitute a first sub-patch image 300a composed of 16×16 pixels around each of the feature points. In addition, the orientation data calculation unit 34 may constitute 4 second sub-patch images 300b each composed of 8×8 pixels and obtained by quartering the first sub-patch image 300a. In addition, the orientation data calculation unit 34 may constitute 16 third sub-patch images 300c each composed of 4×4 pixels and obtained by dividing the first sub-patch image 300a into 16 equal parts.

For all pixels in each of the sub-patch images, the orientation data calculation unit 34 may calculate the Gradient directions $\theta(x, y)$ and the magnitudes $m(x, y)$ using the above equation, and the set $\{m(x, y), \theta(x, y)\}$ obtained by adding up the magnitudes $m(x, y)$ of pixels having similar Gradient directions $\theta(x, y)$ in each of the sub-patch images may be used as orientation data of the corresponding sub-patch The bad feature point removal unit 38 may locate feature points for comparison by removing bad feature points from the feature point obtained from the ultrasound image. In other words, the bad feature point removal unit 38 may locate feature points for comparison by removing bad feature points from the feature points detected from the ultrasound image.

Referring to FIG. 1 and FIG. 2, the bad feature point removal unit 38 may include an edge detector and an edge feature point overlapping determiner. In addition, the bad feature point removal unit 38 may further include an edge width expander 530.

The edge detector 36a may detect edge components included in the ultrasound image.

The edge width expander 530 may generate an edge component through expansion of the width of an edge component detected by the edge detector 36a in the two-dimensional space. When the expanded edge component is used instead of an actual edge component, it is possible to prevent feature points immediately adjacent to the edge component from being removed unfortunately during removal of the bad feature points, thereby providing an advantage in curve fitting and detection of the kidney. In other words, the bad feature point removal unit 38 may remove the bad feature points based on the edge component expanded by the edge width expander 530, whereby the feature points adjacent to the edge component can be used upon curve fitting of the curve fitting unit 46 and the kidney detection unit 48 to detect the kidney (location of the kidney), thereby allowing more accurate detection of the location of the kidney.

The edge feature point overlapping determiner 36b may determine whether the edge component overlaps the feature points of the ultrasound image in the two-dimensional ultrasound image space coordinates.

As a result, the bad feature point removal unit 38 may locate the feature points for comparison from the feature points obtained from the ultrasound image by considering the feature points of the ultrasound image not overlapping the edge component to be the bad feature points. That is, the bad feature points may mean the feature points of the ultrasound image not overlapping the edge component.

In addition, the bad feature point removal unit 38 may include an artificial neural network adapted to perform semantic segmentation to detect the location of the kidney from the ultrasound image. In this case, the bad feature point removal unit 38 may locate the feature points for comparison by training the artificial neural network on template kidney images, performing semantic segmentation with respect to the ultrasound image to detect the kidney region, and removing bad feature points from the feature points obtained from the ultrasound image by the feature point detection unit 32 by considering the feature points of the ultrasound image excluding the feature points in the kidney region subjected to semantic segmentation to be the bad feature points. Here, the ultrasound image subjected to semantic segmentation means the ultrasound image of the patient obtained from the ultrasound probe sensor 30. In other words, the ultrasound image may be the ultrasound image of the patient sent from the ultrasound probe sensor 30. In addition, the feature points in the kidney region subjected to semantic segmentation may mean feature points included in the kidney region subjected to semantic segmentation.

The bad feature points are removed from the ultrasound image by the bad feature point removal unit 38, thereby reducing a calculation burden of the feature point-pair generation unit 42.

The major orientation correction unit 40 may obtain the most frequent orientation as a major rotational orientation in a histogram indicating the frequency of pixels with respect to an orientation, based on the orientation data with respect to the pixels in the patch image of each of the feature points for comparison from the patch image of each of the feature points for comparison. In addition, the major orientation correction unit 40 may correct orientations of the pixels in the patch image of each of the feature points for comparison based on the major rotational orientation.

Herein, for example, the major orientation correction unit 40 may determine the most frequent orientation, as the major rotational orientation, in a histogram showing accumulation of magnitudes m(x, y) of 256 pixels included in the first sub-patch image based on orientation data with respect to the 256 pixels of the first sub-patch image. Here, the major rotational orientation may mean an orientation having the maximum value in the histogram. That is, the major rotational orientation may mean an orientation corresponding to a bar having the maximum area in the histogram.

Herein, major orientation correction may be performed by subtracting the major rotational orientation from the orientation θ(x, y). In other words, the major orientation correction unit 40 may perform the major orientation correction by subtracting the major rotational orientation from the orientation θ(x, y) of the pixels of the patch images of the feature points for comparison. After correction of the orientations of the pixels in the patch image of each of the feature point for comparison by the major orientation correction unit 40, the major orientation of the patch images of the feature points for comparison becomes 0 degrees (0°).

Herein, the orientation data of the template kidney feature points, the template kidney periphery feature points, the feature points of regions of interest of a patient having a normal fatty liver (feature points of regions of interest of a template ultrasound picture having a normal grade of steatosis), and the template diaphragm feature points may be used after correction of the major rotational orientation to 0 degrees (0°).

The feature point-pair generation unit 42 may generate a pair of feature points between the template kidney periphery feature points and the feature points for comparison pertaining to patch images having high similarity through comparison between the orientation data with respect to the pixels in the patch images of the template kidney periphery feature points and in the patch images of the feature points for comparison.

In other words, the feature point-pair generation unit 42 may generate the pair of feature points between the corresponding feature points having a preset degree of similarity or more through comparison between the orientation data with respect to the pixels in the patch images of the template kidney periphery feature points and in the patch images of the feature points for comparison. The method of determining similarity between the orientation data is described above and thus detailed description thereof will be omitted.

On the other hand, the feature points for comparison paired with the template kidney periphery feature points by the feature point-pair generation unit 42 may be referred to as final feature points.

The curve fitting unit 46 may generate a first fitting curve through ellipse fitting or curve fitting with respect to an imaginary closed loop formed by connecting the feature points for comparison (final feature points) paired with the template kidney periphery feature points by the feature point-pair generation unit 42, or may calculating the number of fitting feature points corresponding to the number of feature points overlapping each other on the two-dimensional space coordinates through scanning comparison between a template edge component and the feature points for comparison paired with the template kidney periphery feature points by the feature point-pair generation unit 42.

In addition, the curve fitting unit 46 may calculating the number of fitting feature points corresponding to the number of feature points overlapping each other on the two-dimensional space coordinates through scanning comparison between the template edge component comprising the template kidney periphery feature points and the feature points for comparison paired with the template kidney periphery feature points by the feature point-pair generation unit 42.

Herein, the template edge may mean an edge component comprising all feature points of the kidney periphery in the template ultrasound pictures. On the other hand, the width of the template edge may be set to be greater than an actual edge width in consideration of various changes of the ultrasound image (variation possibility), that is, diversity thereof. In this case, detection of the kidney may be performed more advantageously upon scanning than the case of using the actual edge width.

On the other hand, ellipse fitting and curve fitting may be performed by various ellipse fitting and curve fitting algorithms that are developed or will be developed in the art.

The kidney detection unit 48 may detect the location of the kidney from the ultrasound image based on the first fitting curve or the number of fitting feature points.

Referring to FIG. 1 and FIG. 2, the kidney detection unit 48 may include a fitting distance calculator 48b and a fitting similarity determiner 48a.

The fitting distance calculator 48b may calculate, as a fitting distance, a Euclidean distance between the first fitting curve and the feature points for comparison applied to fitting. Here, the feature points for comparison applied to fitting may mean the feature points for comparison (final feature points) paired with the template kidney periphery feature points by the feature point-pair generation unit 42. That is, the feature points for comparison applied to fitting may mean the feature points for comparison forming the imaginary closed loop through ellipse fitting or curve fitting.

The fitting similarity determiner 48a may determine the degree of similarity with respect to the fitting curve based on the fitting distance.

For example, if the Euclidean distance calculated by the fitting distance calculator 48b is greater than a predetermined value, the fitting similarity determiner 48a may determine that there is no image of the kidney region in the ultrasound image. In other words, if it is determined by the fitting similarity determiner 48a that fitting similarity between the first fitting curve and the feature points for comparison applied to fitting is high, the kidney detection unit 48 may determine that a kidney is present in the ultrasound image. In another embodiment, if it is determined that that a diameter of the first fitting curve, lengths of a major axis and a minor axis or the shape of the fitting curve is similar to the template kidney periphery, the kidney detection unit 48 may determine that a kidney is present in the ultrasound image.

In addition, the fitting distance calculator 48b may calculate, as a fitting distance, a Euclidean distance between the first fitting curve and a second fitting curve obtained by curve fitting with respect to an imaginary closed loop formed by connecting the template kidney periphery feature points. Here, the feature points for comparison applied to fitting may mean the feature points for comparison (final feature points) paired with the template kidney periphery feature points by the feature point-pair generation unit 42. Here, the fitting similarity determiner 48*a* may determine similarity between the first fitting curve and the second fitting curve based on the fitting distance.

Here, the sum of Euclidean distances between the first fitting curve and the feature points for comparison applied to generation of the first fitting curve or the sum of Euclidean distances between the first fitting curve and the second fitting curve may be used in determination of fitting similarity. A lower sum of the Euclidean distances may indicate higher fitting similarity. On the other hand, the method of determining fitting similarity is described above and thus detailed description thereof will be omitted.

Further, the kidney detection unit 48 may detect the location of the kidney from the ultrasound image based on the number of fitting feature points. Here, the number of fitting feature points means the number of feature points overlapping each other on the two-dimensional space coordinates obtained through scanning comparison between the feature points for comparison (final feature points) paired with the template kidney periphery feature points by the feature point-pair generation unit 42 and the template edge component.

The kidney detection unit 48 may determine that that a kidney is present at a coordinate location at which the number of fitting feature points is a predetermined number or more and reaches the maximum value.

The region-of-interest extraction unit 50 may extract images of one or more regions of interest through space addressing on the ultrasound image with reference to the detected kidney (location of the kidney).

Herein, space addressing refers to a process of detecting the location of an organ (organ region), such as the liver, the kidney, and the like, to be observed, based on correlation between physical space locations on the human body with reference to the location of the kidney, when the location of the kidney is determined in the ultrasound image.

Herein, the region of interest may be at least one selected from the group of a liver cortex region, a kidney cortex region, a right portal vein (RPV) region, a hepatic vein region, a spleen region, a diaphragm region, a kidney renal pelvis region, and a kidney renal sinus region in the ultrasound image. In other words, the region of interest may be at least one image region selected from the group of an image of the liver cortex region, an image of the kidney cortex region, an image of the right portal vein (RPV) region, an image of the hepatic vein region, an image of the spleen region, an image of the diaphragm region, an image of the kidney renal pelvis region, and an image of the kidney renal sinus region.

The fatty liver grade determination unit 58 may automatically determine the grade of liver steatosis based on the ultrasound image of a patient input from the ultrasound probe sensor 30.

The fatty liver grade determination unit 58 may include the image integration unit 52 and the artificial neural network 54.

The image integration unit 52 may generate one integrated image through concatenation of images of the regions of interest in the template ultrasound pictures or in the ultrasound image into one integrated image.

The artificial neural network 54 may be trained on the integrated image through deep learning.

The automatic ultrasound diagnosis apparatus 600 according to the embodiments of the invention may automatically determine the grade of liver steatosis of a patient based on the integrated image obtained (acquired) from the ultrasound image of the patient input from the ultrasound probe sensor 30 using the artificial neural network 54 trained through deep learning.

Further, referring to FIG. 2, the automatic ultrasound diagnosis apparatus 600 may include the template feature point statistical data storage unit 57 and the feature point statistical data calculation unit 56.

The template feature point statistical data storage unit 57 may store statistical data with respect to the feature points of the kidney region in the template ultrasound pictures and the feature points of the regions of interest excluding the kidney region. The statistical data stored in the template feature point statistical data storage unit 57 may mean template feature point statistical data.

The feature point statistical data calculation unit 56 may calculate the feature point statistical data from the feature points of the kidney region detected by the kidney detection unit 48 or from the feature points of the regions of interest extracted by the region-of-interest extraction unit 50.

Here, the feature point statistical data may include at least some selected from the group of the number of feature points included in a certain region designated in the ultrasound image, the number of fitting feature points, a histogram indicating intensity distribution of the feature points, an orientation displacement of the feature points, an average of the orientation data of the feature points, a distribution of the orientation data of the feature points, and a standard deviation of the orientation data of the feature points.

The fatty liver grade determination unit 58 may determine the grade of liver steatosis classified into, for example, a mild grade, a normal grade, a moderate grade, a severe grade, and a cirrhosis grade, based on the template feature point statistical data and the feature point statistical data calculated by the feature point statistical data calculation unit 56. That is, the automatic ultrasound diagnosis apparatus 600 according to this embodiment may automatically determine the grade of liver steatosis based on the feature point statistical data of the feature point obtained from the ultrasound image of the patient input from the ultrasound probe sensor 30.

For example, the fatty liver grade determination unit 58 may determine the grade of liver steatosis through calculation of the ratio of the statistical data included in the kidney cortex or kidney periphery region corresponding to the kidney in the ultrasound image of the patient to the statistical data included in the non-kidney region or the ratio of the number of feature points included in the kidney cortex or kidney periphery region corresponding to the kidney in the ultrasound image of the patient to the number of feature points included in the non-kidney region of the ultrasound image.

More specifically, for example, the fatty liver grade determination unit 58 may use an average of the orientation data of the feature points among the statistical data. That is, the fatty liver grade determination unit 58 may determine the grade of liver steatosis based on the ratio of an average value of the orientations of the feature points in the kidney region (the kidney cortex or kidney periphery region) to an average value of the orientations of the feature points in the non-kidney region.

Alternatively, the fatty liver grade determination unit 58 may determine the grade of liver steatosis based on the ratio of the number of the feature points (kidney feature point) in the kidney region (the kidney cortex or kidney periphery region corresponding to the kidney) of the ultrasound image of the patient to the number of the feature points (kidney feature point) included in the non-kidney region of the ultrasound image. For example, when an ultrasound image of a patient having a normal grade fatty liver is used as a template ultrasound picture, the fatty liver grade of the patient may be determined by gradually increasing the grade of liver steatosis to, for example, a mild grade, a moderate grade, and a severe grade, with increasing difference between the ultrasound image of the patient and the template ultrasound picture in terms of the ratio of the number of kidney feature points to the number of non-kidney feature points. That is, a higher difference between the ultrasound image of the patient and the template ultrasound picture corresponding to the normal fatty liver grade (in terms of the ratio of the number of kidney feature points to the number of non-kidney feature points) may mean a higher difference between the liver fatty grade of the patient and the normal liver fatty grade (a liver fatty grade approaching cirrhosis grade).

In addition, the automatic ultrasound diagnosis apparatus 600 according to the embodiments of the invention may further include a template region-of-interest orientation displacement storage unit. The template region-of-interest orientation displacement storage unit may obtain candidate orientations having the maximum magnitudes from each of patch images of feature points of regions of interest in template ultrasound pictures having a normal grade of liver steatosis and may store orientation displacement data corresponding to an orientation difference between the maximum orientation and the minimum orientation among the candidate orientations. Herein, the orientation displacement data may be defined as a difference between the maximum orientation and the minimum orientation among the candidate orientations provided by the Gradient direction $\theta(x, y)$ of the pixels having the maximum magnitudes $m(x, y)$ from each of patch images. The orientation displacement data may mean the range of orientation displacement.

The fatty liver grade determination unit 58 may detect the feature points pertaining to the regions of interest in the ultrasound image of the patient and may determine the fatty liver grade based on the number of fatty liver feature points, as an indicator, corresponding to feature points, which are included in the regions of interest in the ultrasound image of the patient and deviate from the range of the orientation displacement stored in the template region-of-interest orientation displacement storage unit.

It is apparent that a higher fatty liver grade provides a more significant variation in the number of fatty liver feature points in a region of interest than a normal grade ultrasound image. In other words, a greater number of fatty liver feature points may be determined to be a higher fatty liver grade. For reference, the fatty liver grade may increase in the sequence of a mild grade, a normal grade, a moderate grade, a severe grade, and a cirrhosis grade.

For example, when a liver region is set to the region of interest, the automatic ultrasound diagnosis apparatus 600 according to this embodiment may further include a template liver orientation displacement storage unit. The template liver orientation displacement storage unit may obtain candidate orientations having the maximum magnitudes from each of patch images of feature points pertaining to the liver region in template ultrasound pictures having a normal grade of liver steatosis and may store orientation displacement data corresponding to an orientation difference between the maximum orientation and the minimum orientation among the candidate orientations. The fatty liver grade determination unit 58 may detect the feature points of the liver region in the ultrasound image of the patient and may determine the grade of liver steatosis based on the number of fatty liver feature points corresponding to the feature points, which are included in the liver region of the ultrasound image of the patient and deviate from the range of the orientation displacement stored in the template liver orientation displacement storage unit.

Referring to FIG. 7, the automatic ultrasound diagnosis apparatus 600 according to another embodiment may include an ultrasound probe sensor 30, a template diaphragm feature point orientation data storage unit 44a, a template diaphragm orientation displacement storage unit 38a, a feature point detection unit 32, an orientation data calculation unit 34, a bad feature point removal unit 38, a major orientation correction unit 40, a feature point-pair generation unit 42a, a curve fitting unit 46a, a diaphragm image extraction unit 62, a fitting distance calculator 48c, a region-of-interest image extraction unit 60, and a fatty liver grade determination unit 58a.

The automatic ultrasound diagnosis apparatus 600 according to this embodiment may include the same components as or similar components to the components of the embodiments described above and repeated descriptions thereof will be omitted.

The template diaphragm feature point orientation data storage unit 44a may store orientation data with respect to feature points of the diaphragm in template ultrasound pictures and pixels in a patch image of each of the feature points. For example, the feature points of the diaphragm may mean feature points in a diaphragm region or feature points of a diaphragm periphery.

The template diaphragm orientation displacement storage unit 38a may obtain candidate orientations having the maximum magnitudes from each of the patch images corresponding to the template diaphragm feature points and may store orientation displacement data corresponding to a difference between the maximum orientation and the minimum orientation among the candidate orientations as the range of template diaphragm orientation displacement. In other words, the template diaphragm orientation displacement storage unit 38a may obtain the candidate orientations having the maximum magnitudes from each of patch images of the feature points pertaining to the diaphragm region in template ultrasound pictures having a normal grade of liver steatosis to store orientation displacement data corresponding to a difference between the maximum orientation and the minimum orientation among the candidate orientations. Here, the orientation displacement data stored in the template diaphragm orientation displacement storage unit 38a may mean the range of template diaphragm orientation displacement.

The bad feature point removal unit 58a may remove bad feature points from the feature points obtained from the ultrasound image to locate feature points for comparison by considering the feature points of the ultrasound image deviating from a template diaphragm orientation displacement range to be the bad feature points. In other words, the bad feature point removal unit 58a may remove the bad feature points from the feature points of the ultrasound image to locate the feature points for comparison by considering feature points of the ultrasound image including a predetermined ratio or more of pixels in a patch image deviating from a template diaphragm orientation displacement range to be the bad feature points. That is, the patch image of the bad feature points may include a predetermined ratio of pixels having orientation data deviating from the template diaphragm orientation displacement (not included in the template diaphragm orientation displacement).

The feature point-pair generation unit 42a may generate a pair of feature points between the template diaphragm feature points and the feature points for comparison using patch images having high similarity through comparison between the orientation data with respect to the pixels in the patch images of the template diaphragm feature points and in the patch images of the feature points for comparison. In other words, the feature point-pair generation unit 42a may generate the pair of feature points between the feature points using patch images having similarity higher than or equal to a preset degree of similarity through comparison between the orientation data with respect to the pixels in the patch images of the template diaphragm feature points and in the patch images of the feature points for comparison.

The curve fitting unit 46a may generate a two-dimensional curve fitting curve through curve fitting with respect to an imaginary curve formed by connecting the feature points for comparison paired with the template diaphragm feature points by the feature point-pair generation unit 42a.

The diaphragm image extraction unit 62 may extract a diaphragm region image from the two-dimensional curve fitting curve.

The fitting distance calculator 48c may calculate a Euclidean distance between the two-dimensional curve fitting curve and the feature points for comparison applied to curve fitting.

The region-of-interest image extraction unit 60 may extract images of regions of interest from the ultrasound image through detection of locations of the regions of interest based on a location of the image of the diaphragm region extracted by the diaphragm image extraction unit 62. For example, when a liver region is set as the region of interest, the region-of-interest image extraction unit 60 may be the liver region image extraction unit 60. Accordingly, the liver region image extraction unit 60 may extract an image of the liver region from the ultrasound image through detection of the location of the liver region based on the location of the image of the diaphragm region.

The fatty liver grade determination unit 58a may determine the grade of liver steatosis, such as a mild grade, a moderate grade, and a severe grade, based on a "brightness ratio of the region of interest to the diaphragm region" obtained by calculating an average brightness of pixels in the extracted image of the region of interest and an average brightness of pixels in the extracted image of the diaphragm region. Herein, the region of interest may mean an image of the region of interest extracted by the region-of-interest image extraction unit 60 and the diaphragm region may mean an image of the diaphragm region extracted by the diaphragm image extraction unit 62.

For example, when a liver region is set as the region of interest, the "brightness ratio of the region of interest to the diaphragm region" may be the "brightness ratio of the liver region to the diaphragm region". Here, since the liver having a severe grade of liver steatosis generally has a much higher brightness in the pixels of the liver region than the liver having a mild grade of liver steatosis, the "brightness ratio of the liver region to the diaphragm region" can increase. On the other hand, it should be understood that the region of interest is not limited to the liver region in determination of the grade of liver steatosis.

On the other hand, referring to FIG. 9, a remote medical diagnosis system 700 may include an ultrasound medical device 3, an automatic ultrasound diagnosis apparatus 600, a user terminal 400, a communication interface 602, and a medical expert terminal 200.

The ultrasound medical device 3 may be provided with an ultrasound probe sensor 30. The wireless transmitter 3a may be integrated into the ultrasound medical device 3 to wirelessly transmit medical image data of a patient measured by the ultrasound medical device 3.

The automatic ultrasound diagnosis apparatus 600 may mean the apparatus for automatic ultrasound diagnosis of liver steatosis using feature points in an ultrasound image according to the embodiments of the present invention. The automatic ultrasound diagnosis apparatus 600 may receive an ultrasound image of the patient sent from the wireless transmitter 3a and automatically determine the grade of liver steatosis.

The user terminal 400 may include a camera 61, a first authentication unit 67, a recording unit 63, an internet connector 64, and a first consultation service unit 65. Here, the camera 61 may monitor use of the ultrasound medical device 3. The first authentication unit 67 may wirelessly authenticate a product ID of the ultrasound medical device 3. The recording unit 63 may store the ultrasound image of the patient acquired by the ultrasound medical device 3. The internet connector 64 may transmit the ultrasound image and the product ID of the ultrasound medical device 3 to a remote diagnosis server 203 via a communication network 202 and may provide a communication channel for a remote consultation service. The first consultation service unit 65 may provide a consultation service with a medical expert.

The communication interface 602 may provide a connection to the automatic ultrasound diagnosis apparatus 600 and the user terminal 400.

The user terminal 400 may further include an artificial neural network 70 and a virtual doctor 79 including a guide unit 71 and a diagnosis unit 72. Here, the artificial neural network 70 and the virtual doctor 79 may reside as software in the user terminal 400.

The artificial neural network 70 may be trained on a medical image database accumulated by the ultrasound medical device 3 by deep learning.

The guide unit 71 may guide or instruct how to use the ultrasound medical device 3 and the diagnosis unit 72 and may output a diagnostic result obtained through automatic analysis of the fatty liver grade determination unit 58 based on the medical image data of the patient acquired by the ultrasound medical device 3.

The medical expert terminal 200 may include a receiver (not shown) and a second consultation service unit (not shown). The receiver (not shown) may receive the medical image data or the ultrasound image via the communication network 80 and the second consultation service unit (not shown) may provide a consultation service between a user and a medical expert.

Next, a remote medical diagnosis method according to one embodiment of the present invention (hereinafter referred to as the remote medical diagnosis method) will be briefly described based on the above description. The remote medical diagnosis method may be implemented based on various embodiments of the automatic ultrasound diagnosis apparatus 600 and the remote medical diagnosis system 700. Accordingly, the descriptions of the automatic ultrasound diagnosis apparatus 600 and the remote medical diagnosis system 700 may also be applied to the remote medical diagnosis method.

The remote medical diagnosis method may include the steps of extracting feature points from an ultrasound image of a patient; removing bad feature points from the feature points to obtain (acquire) feature points for comparison; detecting a location of a kidney based on the feature points on the ultrasound image; extracting images of one or more regions of interest through space addressing on the ultrasound image of the patient with reference to the detected kidney (location of the kidney); determining, by the virtual doctor 79, a grade of liver steatosis of the patient based on the images of the regions of interest; and performing, by the remote medical diagnosis system 700, a remote consultation service with a medical expert.

It should be understood that each of the steps of the remote medical diagnosis method may be divided into additional steps or may be combined with each other according to implementations of the present invention. Further, in the remote medical diagnosis method, some steps may be omitted and the sequence of the steps may be changed, as needed.

The remote medical diagnosis method may be realized in the form of program instructions which can be implemented through various computer components, and may be recorded in a computer-readable storage medium. The computer-readable storage medium may include program instructions, a data file, a data structure, and the like either alone or in combination thereof. The program instructions recorded in the computer-readable storage medium may be any program instructions particularly designed and structured for the present invention or known to those skilled in the field of computer software. Examples of the computer-readable storage medium include magnetic recording media, such as hard disks, floppy disks and magnetic tapes, optical data storage media, such as CD-ROMs and DVD-ROMs, magneto-optical media such as floptical disks, and hardware devices, such as read-only memories (ROMs), random-access memories (RAMs), and flash memories, which are particularly structured to store and implement the program instructions. Examples of the program instructions include not only assembly language code formatted by a compiler but also high-level language code which can be implemented by a computer using an interpreter. The hardware device described above may be configured to operate as one or more software modules to perform operations of the present invention, and vice versa.

In addition, the remote medical diagnosis method may be implemented in the form of a computer-executable computer program or application stored in a recording medium.

Although some embodiments have been described herein, it should be understood that these embodiments are provided for illustration and that various modifications, changes, alterations, and equivalent embodiments can be made by those skilled in the art without departing from the spirit and scope of the invention. Therefore, the embodiments are not to be construed in any way as limiting the present invention. For example, each component described as a single type may be implemented in a distributed manner, and, similarly, components described as distributed may be implemented in a combined form.

The scope of the present application should be defined by the appended claims and equivalents thereof rather than by the detailed description, and all changes or modifications derived from the spirit and scope of the claims and equivalents thereof should construed as included in the scope of the present invention.

LIST OF REFERENCE NUMERALS

600: automatic ultrasound apparatus for diagnosis of liver steatosis
30: ultrasound probe sensor
32: feature point detection unit
34: orientation data calculation unit
38: bad feature point removal unit
36*a*: edge detector
36*b*: edge feature point overlapping determiner
40: major orientation correction unit
42: feature point-pair generation unit
44: template kidney feature point orientation data storage unit
46: curve fitting unit
48: kidney detection unit
50: region-of-interest extraction unit
48*a*: fitting similarity determiner
48*b*: fitting distance calculator
56: feature point statistical data calculation unit
57: template feature point statistical data storage unit
58: fatty liver grade determination unit

What is claimed is:

1. An apparatus for automatic ultrasound diagnosis of liver steatosis using feature points in an ultrasound image, the apparatus comprising:

an ultrasound probe sensor acquiring an ultrasound image from a patient;

a template kidney feature point orientation data storage unit storing orientation data with respect to template kidney periphery feature points corresponding to feature points of a kidney periphery in template ultrasound pictures and pixels in a patch image of each of the feature points;

a feature point detection unit detecting feature points from the ultrasound image or from an edge component of the ultrasound image;

an orientation data calculation unit calculating orientation data with respect to pixels in a patch image of each of the feature points of the ultrasound image;

a bad feature point removal unit removing bad feature points from the feature points of the ultrasound image to locate feature points for comparison;

a major orientation correction unit obtaining the most frequent orientation as a major rotational orientation in a histogram indicating the frequency of pixels with respect to an orientation, based on orientation data with respect to pixels in a patch image of each of the feature points for comparison, and correcting orientations of the pixels in the patch image of each of the feature points for comparison based on the major rotational orientation;

a feature point-pair generation unit generating a pair of feature points between the template kidney periphery feature points and the feature points for comparison pertaining to patch images having high similarity through comparison between the orientation data with respect to the pixels in the patch images of the template kidney periphery feature points and in the patch images of the feature points for comparison;

a curve fitting unit generating a first fitting curve through ellipse fitting or curve fitting with respect to an imaginary closed loop formed by connecting the feature points for comparison paired with the template kidney periphery feature points by the feature point-pair generation unit, or calculating the number of fitting feature points corresponding to the number of feature points overlapping each other on two-dimensional space coordinates through scanning comparison between a template edge component and the feature points for comparison paired with the template kidney periphery feature points by the feature point-pair generation unit;
a kidney detection unit detecting a location of a kidney from the ultrasound image based on the first fitting curve or the number of fitting feature points;
a region-of-interest extraction unit extracting images of one or more regions of interest through space addressing on the ultrasound image with reference to the detected kidney; and
a fatty liver grade determination unit determining a grade of liver steatosis based on the ultrasound image of the patient input from the ultrasound probe sensor.

2. An apparatus for automatic ultrasound diagnosis of liver steatosis using feature points in an ultrasound image, the apparatus comprising:
an ultrasound probe sensor acquiring an ultrasound image from a patient;
a template kidney feature point orientation data storage unit storing orientation data with respect to template kidney periphery feature points corresponding to feature points of a kidney periphery in template ultrasound pictures and pixels in a patch image of each of the feature points;
a template feature point statistical data storage unit storing statistical data with respect to feature points of a kidney region in the template ultrasound pictures and feature points of regions of interest excluding the kidney region;
a feature point detection unit detecting feature points from the ultrasound image or from an edge component of the ultrasound image;
an orientation data calculation unit calculating orientation data with respect to pixels in a patch image of each of the feature points of the ultrasound image;
a bad feature point removal unit removing bad feature points from the feature points of the ultrasound image to locate feature points for comparison;
a major orientation correction unit obtaining the most frequent orientation as a major rotational orientation in a histogram indicating the frequency of pixels with respect to an orientation, based on orientation data with respect to pixels in a patch image of each of the feature points for comparison, and correcting orientations of the pixels in the patch image of each of the feature points for comparison based on the major rotational orientation
a feature point-pair generation unit generating a pair of feature points between the template kidney periphery feature points and the feature points for comparison pertaining to patch images having high similarity through comparison between the orientation data with respect to the pixels in the patch images of the template kidney periphery feature points and in the patch images of the feature points for comparison;
a curve fitting unit generating a first fitting curve through ellipse fitting or curve fitting with respect to an imaginary closed loop formed by connecting the feature points for comparison paired with the template kidney periphery feature points by the feature point-pair generation unit, or calculating the number of fitting feature points corresponding to the number of feature points overlapping each other on two-dimensional space coordinates through scanning comparison between a template edge component and the feature points for comparison paired with the template kidney periphery feature points by the feature point-pair generation unit;
a kidney detection unit detecting a location of a kidney from the ultrasound image based on the first fitting curve or the number of fitting feature points;
a region-of-interest extraction unit extracting images of one or more regions of interest through space addressing on the ultrasound image with reference to the detected kidney;
a feature point statistical data calculation unit calculating feature point statistical data from the feature points of the kidney region detected by the kidney detection unit or from the feature points of the regions of interest extracted by the region-of-interest extraction unit; and
a fatty liver grade determination unit determining a grade of liver steatosis classified into a mild grade, a moderate grade, a severe grade, and a cirrhosis grade, based on the template feature point statistical data and the feature point statistical data obtained from the feature point statistical data calculation unit,
wherein the grade of liver steatosis of the patient is automatically determined based on the feature point statistical data of the feature points obtained from the ultrasound images of the patient input from the ultrasound image sensor.

3. The apparatus for automatic ultrasound diagnosis of liver steatosis according to claim 1, wherein the kidney detection unit comprises:
a fitting distance calculator calculating, as a fitting distance, a Euclidean distance between the first fitting curve and the feature points for comparison applied to fitting; and
a fitting similarity determiner determining similarity to the fitting curve based on the fitting distance.

4. The apparatus for automatic ultrasound diagnosis of liver steatosis according to claim 1, wherein the kidney detection unit comprises:
a fitting distance calculator calculating, as a fitting distance, a Euclidean distance between the first fitting curve and a second fitting curve obtained by curve fitting with respect to an imaginary closed loop formed by connecting the template kidney periphery feature points; and
a fitting similarity determiner determining similarity between the first fitting curve and the second fitting curve based on the fitting distance.

5. The apparatus for automatic ultrasound diagnosis of liver steatosis according to claim 2, wherein the fatty liver grade determination unit determines the grade of liver steatosis through calculation of a ratio of statistical data included in a kidney cortex or kidney periphery region corresponding to the kidney in the ultrasound image of the patient to statistical data included in a non-kidney region of the ultrasound image or a ratio of the number of feature points included in the kidney cortex or kidney periphery region corresponding to the kidney in the ultrasound image of the patient to the number of feature points included in the non-kidney region of the ultrasound image.

6. The apparatus for automatic ultrasound diagnosis of liver steatosis according to claim 1, wherein the fatty liver grade determination unit comprises:
an image integration unit concatenating images of the regions of interest in the template ultrasound pictures or in the ultrasound image into one integrated image; and
an artificial neural network trained on the integrated image by deep learning, the deep learning-trained artificial neural network being used to automatically determine the grade of liver steatosis of the patient based on the integrated image obtained from the ultrasound image of the patient input from the ultrasound probe sensor.

7. An apparatus for automatic ultrasound diagnosis of liver steatosis using feature points in an ultrasound image, the apparatus comprising:
- an ultrasound probe sensor acquiring an ultrasound image from a patient;
- a template diaphragm feature point orientation data storage unit storing orientation data with respect to template diaphragm feature points corresponding to feature points of the diaphragm included in template ultrasound pictures and pixels in a patch image of each of the feature points;
- a template diaphragm orientation displacement storage unit obtaining candidate orientations having the maximum magnitudes from each of the patch images corresponding to the template diaphragm feature points and storing, as template diaphragm orientation displacement data, orientation displacement data corresponding to a difference between the maximum orientation and the minimum orientation among the candidate orientations;
- a feature point detection unit detecting feature points in the ultrasound image;
- an orientation data calculation unit calculating orientation data with respect to pixels in a patch image of each of the feature points of the ultrasound image;
- a bad feature point removal unit removing bad feature points from the feature points obtained from the ultrasound image to locate feature points for comparison, the bad feature points being determined by considering feature points of the ultrasound image deviating from a template diaphragm orientation displacement range to be the bad feature points;
- a major orientation correction unit obtaining the most frequent orientation as a major rotational orientation in a histogram indicating the frequency of pixels with respect to an orientation, based on orientation data with respect to pixels in a patch image of each of the feature points for comparison, and correcting orientations of the pixels in the patch image of each of the feature points for comparison based on the major rotational orientation;
- a feature point-pair generation unit generating a pair of feature points between the feature points using patch images having high similarity through comparison between the orientation data with respect to the pixels in the patch images of the template diaphragm feature points and in the patch images of the feature points for comparison;
- a curve fitting unit generating a two-dimensional curve fitting curve through curve fitting with respect to an imaginary closed loop formed by connecting the feature points for comparison paired with the template diaphragm feature points by the feature point-pair generation unit;
- a diaphragm image extraction unit extracting an image of a diaphragm region from the two-dimensional curve fitting curve;
- a fitting distance calculator calculating a Euclidean distance between the two-dimensional curve fitting curve and the feature points for comparison applied to curve fitting;
- a region-of-interest image extraction unit extracting an image of a region of interest from the ultrasound image through detection of a location of the region of interest based on a location of the extracted image of the diaphragm region; and
- a fatty liver grade determination unit determining a grade of liver steatosis classified into a mild grade, a moderate grade, a severe grade, and a cirrhosis grade, based on a brightness ratio of the region of interest to the diaphragm region obtained by calculating an average brightness of pixels in the extracted image of the region of interest and an average brightness of pixels in the extracted image of the diaphragm region,
- wherein the grade of liver steatosis of the patient is automatically determined based on the brightness ratio of the region of interest to the diaphragm region obtained from the ultrasound image of the patient input from the ultrasound probe sensor.

8. The apparatus for automatic ultrasound diagnosis of liver steatosis according to claim 1, wherein the region of interest is at least one selected from the group of a liver cortex region, a kidney cortex region, a right portal vein (RPV) region, a hepatic vein region, a spleen region, a diaphragm region, a kidney renal pelvis region, and a kidney renal sinus region in the ultrasound image.

9. The apparatus for automatic ultrasound diagnosis of liver steatosis according to claim 1, wherein the bad feature point removal unit comprises:
- an edge detector adapted to detect the edge component of the ultrasound image;
- an edge width expander adapted to generate an edge component having an expanded width through expansion of a width of the edge component in a two-dimensional space; and
- an edge feature point overlapping determiner adapted to determine whether the edge component overlaps the feature points of the ultrasound image on two-dimensional ultrasound image space coordinates to locate the feature points for comparison through removal of the bad feature points from the feature points of the ultrasound image, the bad feature points being determined by considering feature points of the ultrasound image not overlapping the edge component to be the bad feature points.

10. The apparatus for automatic ultrasound diagnosis of liver steatosis according to claim 1, wherein the bad feature point removal unit comprises an artificial neural network performing semantic segmentation to detect the location of the kidney from the ultrasound image, and locates the feature points for comparison by training the artificial neural network on template kidney images, detecting a kidney region through semantic segmentation of the ultrasound image, and removing the bad feature points from the feature points obtained from the ultrasound image of the patient by the feature point detection unit, the bad feature points being determined by considering the feature points of the ultrasound image excluding feature points in the kidney region detected through semantic segmentation to be the bad feature points.

11. An apparatus for automatic ultrasound diagnosis of liver steatosis, comprising:
- an ultrasound medical device provided with an ultrasound probe sensor;
- a wireless transmitter integrated into the ultrasound medical device to wirelessly transmit medical image data of a patient measured by the ultrasound medical device;

the automatic ultrasound diagnosis apparatus according to claim 1, the automatic ultrasound diagnosis apparatus receiving an ultrasound image of the patient from the wireless transmitter 3a and automatically determining a grade of liver steatosis;

a user terminal comprising a camera monitoring use of the ultrasound medical device, a first authentication unit wirelessly authenticating a product ID of the ultrasound medical device, a recording unit storing the ultrasound image of the patient obtained by the ultrasound medical device, an Internet connector transmitting the ultrasound image and the product ID of the ultrasound medical device to a remote diagnosis server via a communication network and providing a communication channel for a remote consultation service, and a first consultation service unit providing a consultation service with a medical expert;

a communication interface providing a connection to the automatic ultrasound diagnosis apparatus and the user terminal;

an artificial neural network residing as software in the user terminal and trained on a medical image database accumulated by the ultrasound medical device by deep learning;

a virtual doctor residing as software in the user terminal, the virtual doctor comprising a guide unit guiding or instructing how to use the ultrasound medical device and a diagnosis unit outputting a diagnostic result obtained through automatic analysis of the medical image data of the patient obtained by the ultrasound medical device using the deep learning-trained artificial neural network; and a medical expert terminal comprising a receiver receiving the medical image data and the ultrasound image via the communication network and a second consultation service unit providing a consultation service between a user and a medical expert.

12. A remote medical diagnosis method using the apparatus for automatic ultrasound diagnosis of liver steatosis according to claim 11, the method comprising:

extracting feature points from an ultrasound image of a patient;

removing bad feature points from the feature points to locate feature points for comparison;

detecting a location of a kidney based on the feature points on the ultrasound image;

extracting images of one or more regions of interest through space addressing on the ultrasound image of the patient with reference to the detected kidney;

determining, by the virtual doctor, a grade of liver steatosis of the patient based on the images of the regions of interest; and performing, by the remote medical diagnosis system, a remote consultation service with a medical expert.

13. The apparatus for automatic ultrasound diagnosis of liver steatosis according to claim 2, wherein the kidney detection unit comprises:

a fitting distance calculator calculating, as a fitting distance, a Euclidean distance between the first fitting curve and the feature points for comparison applied to fitting; and a fitting similarity determiner determining similarity to the fitting curve based on the fitting distance.

14. The apparatus for automatic ultrasound diagnosis of liver steatosis according to claim 2, wherein the kidney detection unit comprises:

a fitting distance calculator calculating, as a fitting distance, a Euclidean distance between the first fitting curve and a second fitting curve obtained by curve fitting with respect to an imaginary closed loop formed by connecting the template kidney periphery feature points; and a fitting similarity determiner determining similarity between the first fitting curve and the second fitting curve based on the fitting distance.

15. The apparatus for automatic ultrasound diagnosis of liver steatosis according to claim 2, wherein the region of interest is at least one selected from the group of a liver cortex region, a kidney cortex region, a right portal vein (RPV) region, a hepatic vein region, a spleen region, a diaphragm region, a kidney renal pelvis region, and a kidney renal sinus region in the ultrasound image.

16. The apparatus for automatic ultrasound diagnosis of liver steatosis according to claim 6, wherein the region of interest is at least one selected from the group of a liver cortex region, a kidney cortex region, a right portal vein (RPV) region, a hepatic vein region, a spleen region, a diaphragm region, a kidney renal pelvis region, and a kidney renal sinus region in the ultrasound image.

17. The apparatus for automatic ultrasound diagnosis of liver steatosis according to claim 7, wherein the region of interest is at least one selected from the group of a liver cortex region, a kidney cortex region, a right portal vein (RPV) region, a hepatic vein region, a spleen region, a diaphragm region, a kidney renal pelvis region, and a kidney renal sinus region in the ultrasound image.

18. The apparatus for automatic ultrasound diagnosis of liver steatosis according to claim 2, wherein the bad feature point removal unit comprises:

an edge detector adapted to detect the edge component of the ultrasound image;

an edge width expander adapted to generate an edge component having an expanded width through expansion of a width of the edge component in a two-dimensional space; and an edge feature point overlapping determiner adapted to determine whether the edge component overlaps the feature points of the ultrasound image on two-dimensional ultrasound image space coordinates to locate the feature points for comparison through removal of the bad feature points from the feature points of the ultrasound image, the bad feature points being determined by considering feature points of the ultrasound image not overlapping the edge component to be the bad feature points.

19. The apparatus for automatic ultrasound diagnosis of liver steatosis according to claim 2, wherein the bad feature point removal unit comprises an artificial neural network performing semantic segmentation to detect the location of the kidney from the ultrasound image, and locates the feature points for comparison by training the artificial neural network on template kidney images, detecting a kidney region through semantic segmentation of the ultrasound image, and removing the bad feature points from the feature points obtained from the ultrasound image of the patient by the feature point detection unit, the bad feature points being determined by considering the feature points of the ultrasound image excluding feature points in the kidney region detected through semantic segmentation to be the bad feature points.

* * * * *